United States Patent
Bakos

(10) Patent No.: US 8,348,834 B2
(45) Date of Patent: Jan. 8, 2013

(54) STEERABLE SURGICAL ACCESS DEVICES AND METHODS

(75) Inventor: Gregory J. Bakos, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1055 days.

(21) Appl. No.: 12/338,125

(22) Filed: Dec. 18, 2008

(65) Prior Publication Data

US 2010/0160735 A1 Jun. 24, 2010

(51) Int. Cl.
*A61B 1/00* (2006.01)

(52) U.S. Cl. ........ 600/142; 600/114; 600/139; 600/140; 600/141

(58) Field of Classification Search .................. 600/139, 600/141–142
See application file for complete search history.

(56) References Cited

U.S. PATENT DOCUMENTS

| | | | | |
|---|---|---|---|---|
| 3,060,972 | A | * | 10/1962 | Sheldon ........................ 138/120 |
| 3,470,876 | A | | 10/1969 | Barchilon |
| 4,580,551 | A | | 4/1986 | Siegmund et al. |
| 4,686,963 | A | * | 8/1987 | Cohen et al. ................... 600/141 |
| 5,005,558 | A | * | 4/1991 | Aomori ......................... 600/141 |
| 5,325,845 | A | | 7/1994 | Adair |
| 5,449,021 | A | | 9/1995 | Chikama et al. |
| 5,807,241 | A | * | 9/1998 | Heimberger .................. 600/142 |
| 5,873,817 | A | | 2/1999 | Kokish et al. |
| 5,904,647 | A | | 5/1999 | Ouchi |
| 5,976,075 | A | | 11/1999 | Beane et al. |
| 6,179,776 | B1 | | 1/2001 | Adams et al. |
| 6,270,453 | B1 | | 8/2001 | Sakai |
| 6,491,626 | B1 | | 12/2002 | Stone et al. |
| 6,672,338 | B1 | | 1/2004 | Esashi et al. |
| 6,749,560 | B1 | | 6/2004 | Konstorum et al. |
| 6,780,151 | B2 | | 8/2004 | Grabover et al. |
| 7,008,375 | B2 | | 3/2006 | Weisel |
| 2004/0138529 | A1 | | 7/2004 | Wiltshire et al. |
| 2004/0186350 | A1 | | 9/2004 | Brenneman et al. |
| 2004/0199052 | A1 | | 10/2004 | Banik et al. |
| 2004/0230095 | A1 | | 11/2004 | Stefanchik et al. |
| 2005/0065401 | A1 | | 3/2005 | Saadat et al. |
| 2005/0124855 | A1 | | 6/2005 | Jaffe et al. |
| 2005/0131279 | A1 | | 6/2005 | Boulais et al. |
| 2005/0228224 | A1 | | 10/2005 | Okada et al. |
| 2006/0015009 | A1 | | 1/2006 | Jaffe et al. |

(Continued)

OTHER PUBLICATIONS

International Search Report for App. No. PCT/US2009/066686 dated Mar. 5, 2010.

*Primary Examiner* — Matthew J Kasztejna
(74) *Attorney, Agent, or Firm* — Nutter McClennen & Fish LLP

(57) ABSTRACT

Methods and devices are provided for controlling movement of a working end of a surgical device configured to be introduced into a body. In one embodiment, a surgical device is provided including a cannulated elongate shaft having a distal working end with a flexible steering platform. The flexible steering platform can includes a plurality of axially aligned links and a plurality of flexible connector elements. Adjacent links can be connected using at least two of the connector elements such that flexing one or more connector elements can bend the steering platform in one or more directions. The surgical device's shaft can be configured to receive a flexible surgical instrument therein such that a working end of the surgical instrument can be received within the steering platform, thereby allowing movement of the surgical instrument's working end to be controlled through movement of the steering platform.

19 Claims, 22 Drawing Sheets

U.S. PATENT DOCUMENTS

| | | | |
|---|---|---|---|
| 2006/0058582 A1* | 3/2006 | Maahs et al. | 600/144 |
| 2006/0178556 A1 | 8/2006 | Hasser et al. | |
| 2006/0178560 A1 | 8/2006 | Saadat et al. | |
| 2007/0049800 A1 | 3/2007 | Boulais | |
| 2007/0225562 A1 | 9/2007 | Spivey et al. | |
| 2009/0270686 A1 | 10/2009 | Duke et al. | |

\* cited by examiner

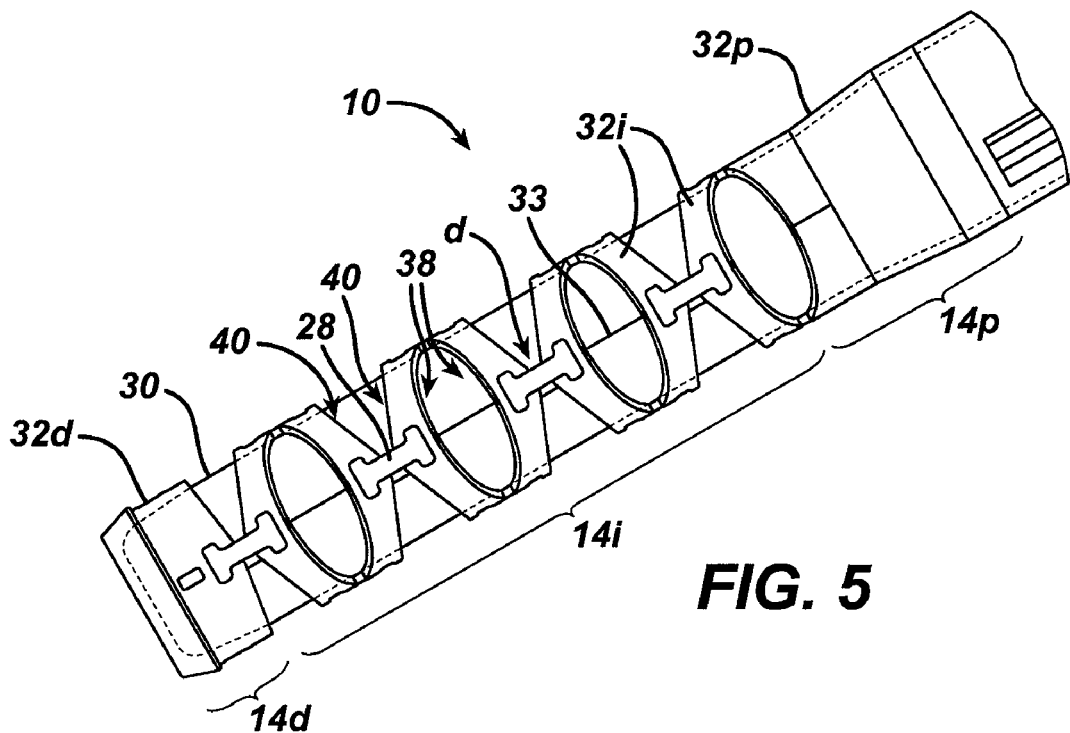
FIG. 5
FIG. 6
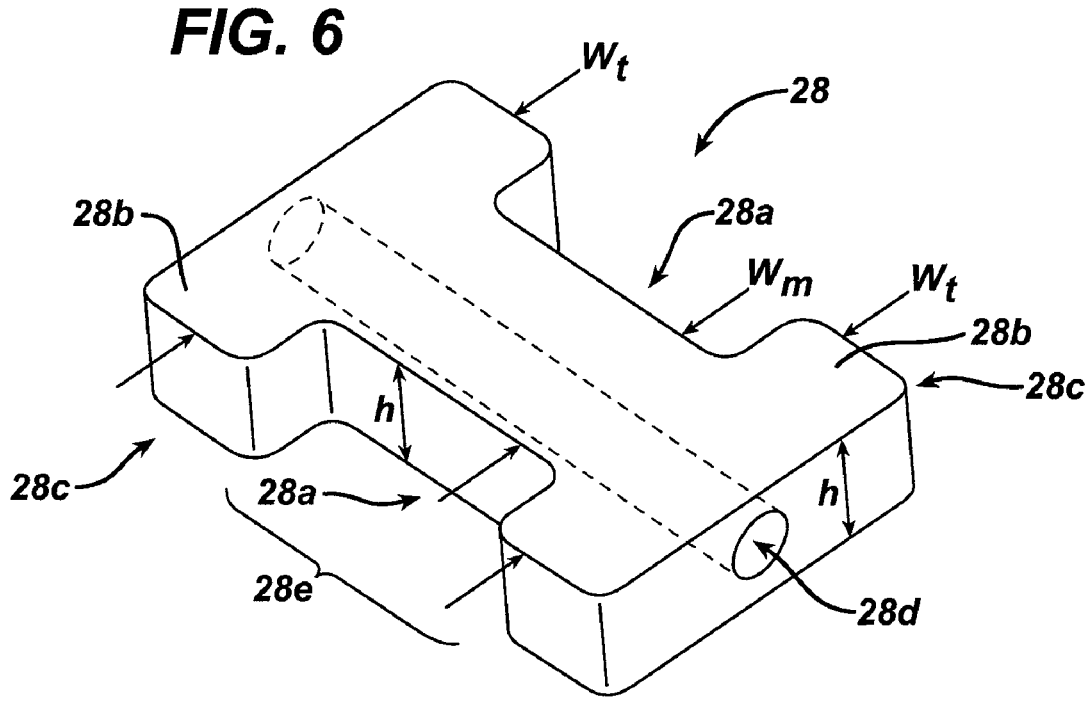

STEERABLE SURGICAL ACCESS DEVICES AND METHODS

FIELD OF THE INVENTION

The present invention relates to devices and methods for controlling movement of a working end of a surgical device.

BACKGROUND OF THE INVENTION

Minimally invasive surgical techniques such as endoscopies and laparoscopies are often preferred over traditional open surgeries because the recovery time, pain, and surgery-related complications are typically less with minimally invasive surgical techniques. Rather than cut open large portions of the body in order to access inner cavities, such as the peritoneal cavity, surgeons either rely on natural orifices of the body or create one or more small orifices in which surgical instruments can be inserted to allow surgeons to visualize and operate at the surgical site. Surgeons can then perform a variety of diagnostic procedures, such as visual inspection or removal of a tissue sample for biopsy, or treatment procedures, such as removal of a polyp or tumor or restructuring tissue.

Because of the rise in popularity of minimally invasive surgeries, there has been significant development with respect to the instruments used in such procedures. These instruments need to be suitable for precise placement of a working end at a desired surgical site to allow the surgeon to see the site and/or perform the necessary actions at such site. Oftentimes the instruments either themselves contain a device that allows the surgeon to see the site or else the instruments are used in conjunction with an instrument that can provide visual assistance. At least one of these types of devices, an endoscope, is typically configured with both a lens to visualize the surgical site and a channel through which instruments can be delivered to the surgical site for subsequent use. The instruments themselves can be used to engage and or treat tissue and other portions within the body in a number of different ways to achieve a diagnostic or therapeutic effect.

Minimally invasive procedures normally require that the shaft of a device inserted into the body be flexible to navigate through and around various shapes within the anatomy while still allowing a working end of the device to be articulated to angularly orient the working end relative to the tissue. During an endoscopy, for example, it is often necessary to navigate a device in a variety of different directions before the device reaches its desired destination, which means it is desirable that any such device be flexible. However, it can be challenging and time-consuming to remotely control a working end of the device such that it can be directed through the varied, tight working spaces of the body to the desired location so that the desired procedures can be performed upon reaching the desired location. It can also be complicated to integrate controls for articulating the working end of the device because of the use of a flexible shaft and the size constraints of such an endoscopic instrument. Further, even when the device reaches its original desired destination, it is often the case that the surgeon will want to move the device during the course of the procedure, such as to make small placement adjustments for visualization purposes. It can thus be desirable for the working end of the device to be adjustable within the body as needed during a surgical procedure.

Accordingly, there remains a need for improved devices and methods for controlling surgical devices used during surgical procedures.

SUMMARY OF THE INVENTION

The present invention generally provides methods and devices for controlling movement of a working end of a surgical device. In one embodiment, a surgical device is provided including a flexible steering platform configured to receive a distal end of a flexible surgical instrument in a central passageway extending through the steering platform. The steering platform has a plurality of links each having a central bore such that the central bores define the central passageway, and a plurality of flexible connector elements. Adjacent links are connected with at least two of the connector elements such that flexing at least two of the connector elements can bend the steering platform in at least two planes of motion. In some embodiments, the at least two planes of motion are substantially perpendicular.

The device can vary in a number of ways. For example, each of the links can include at least one recess, each recess having one of the connector elements disposed therein. As another example, the device can include first and second actuating cables extending at least partially through each of the plurality of links, wherein at least one of the first and second actuating cables extends at least partially through each of the plurality of flexible connector elements. The first actuating cable can be configured to bend the steering platform in a first plane of motion and the second actuating cable can be configured to bend the steering platform in a second plane of motion. In some embodiments, the device can include third and fourth actuating cables extending at least partially through each of the plurality of links, wherein the first, second, third, and fourth actuating cables are spaced equidistantly around the central passageway.

As yet another example, the device can include an elongate body having an inner lumen extending therethrough, wherein the elongate body is connected to a proximal end of the steering platform and the inner lumen is in communication with the central passageway. The steering platform can have a longitudinal length that is in a range of about 15% to 100% a longitudinal length of the elongate body, e.g., about 25%.

In another aspect, a surgical device is provided including a steering segment having an outer sheath disposed over a steering platform. The steering platform can be bendable and have a proximal base ring, a distal end ring, a plurality of separate links located between the proximal base ring and the distal end ring, and a plurality of flexible connector elements. Each of the links can be in the form of a ring, wherein the links are arranged consecutively along a length of the steering segment between the base ring and the end ring so as to define an inner lumen extending through the base ring, the end ring, and the links. At least two of the connector elements can connect adjacent links such that each of the links has at least two connector elements connected thereto.

The device can vary in any number of ways. For example, the steering segment can be bendable in at least four directions. For another example, the proximal base ring can be configured to be removably connected to a distal end of a cannulated elongate body, the elongate body configured to receive a surgical instrument therein. For still another example, the device can include at least one actuating cable extending through the plurality of separate links and the plurality of flexible connector elements. In some embodiments, each link can have at least one link bore formed axially therethrough, each connector element can have at least one connector bore formed axially therethrough, and the link bores and the connector bores can be aligned such that the at least one actuating cable extends through the at least one link bore in each link and through the at last one connector bore in each connector element.

In another aspect, a surgical device is provided including a bendable steering platform configured to receive a distal end of a bendable surgical instrument disposed in a central passageway of the steering platform. The steering platform has a proximal base link having a distal side with at least two opposed concave end surfaces and at least two convex end surfaces, a distal end link having a proximal side with at least two opposed concave end surfaces and at least two opposed convex end surfaces, a plurality of intermediate links located between the proximal base link and the distal end link, and a plurality of flexible connector elements, at least two of the connector elements connecting adjacent links. The base link, the end link, and the intermediate links are linearly arranged. Each of the intermediate links has a proximal side with at least two opposed concave surfaces and at least two convex surfaces and a distal side with at least two opposed concave surfaces and at least two convex surfaces.

The device can have any number of variations. For example, the device can include an actuating cable extending at least partially through each of the plurality of links and each of the plurality of connector elements such that actuating the actuating cable can bend the bendable steering platform such that at least one concave surface on a proximal side of a first one of the links moves toward at least one concave surface on a distal side of a second one of the links that is adjacent to the first one of the links. For another example, the at least two opposed convex surfaces on the proximal sides of the intermediate links can face the at least two opposed convex surfaces on the distal side of an adjacent one of the proximal link or intermediate links. For still another example, the connector elements can couple to convex surfaces of adjacent links. For yet another example, the proximal side and the distal side of adjacent links can be separated by a distance at least when the central passageway is substantially straight. For another example, facing surfaces of adjacent links can contact each other at least when a longitudinal axis of the central passageway is substantially straight. For yet another example, each of the convex surfaces can include a beveled edge configured to engage a beveled edge of an adjacent link when the steering platform bends. For still another example, facing surfaces of adjacent links can be separated by a distance at least when a longitudinal axis of the central passageway is substantially straight. In some embodiments, the facing surfaces of adjacent links can be configured to contact each other when the steering segment bends.

In another aspect, a surgical method is provided including introducing a surgical instrument having a steering segment at a distal end thereof into a patient. The steering segment can include a plurality of links each having first and second holes formed in a wall thereof, a plurality of axially aligned flexible connector elements each having first bores formed therethrough, a first actuating cable extending through each of the bores and the first holes, and a second actuating cable extending through each of the second holes. At least two of the plurality of connector elements can connect adjacent ones of the plurality of links such that the bores of the connector elements align with the first holes of the links. The method also includes actuating at least one of the actuating cables to bend the steering segment and the distal end of the surgical instrument.

The method can vary in any number of ways. For example, introducing a steering segment into a patient can include transorally introducing the steering segment into the patient. For another example, the method can also include actuating the first and second actuating cables to bend the steering segment in at least two planes of motion.

BRIEF DESCRIPTION OF THE DRAWINGS

The invention will be more fully understood from the following detailed description taken in conjunction with the accompanying drawings, in which:

FIG. 5 is another perspective view of the distal end of the device of FIG. 1 including the steering platform and a portion of the shaft with the device in a resting position;

FIG. 6 is a perspective transparent view of a connector element included in the steering platform of FIG. 1;

DETAILED DESCRIPTION OF THE INVENTION

Figure 1:
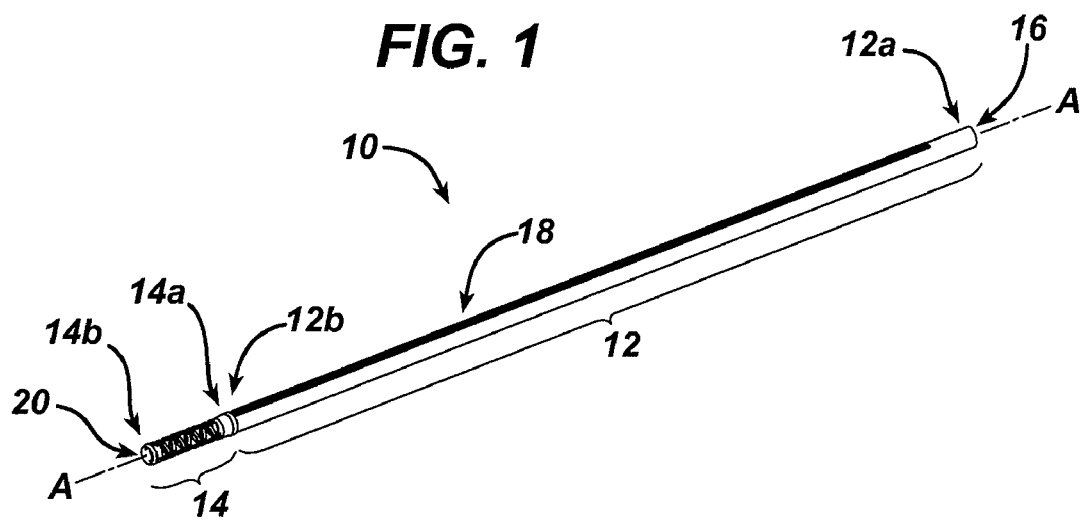
FIG. 1 is a perspective view of one embodiment of a surgical device including an elongate shaft and an articulating steering platform extending distally from the shaft.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for controlling movement of a working end of a surgical device configured to be introduced into a body. In general, a surgical device is provided including a cannulated elongate shaft having a distal working end with a flexible steering platform, and a proximal end with a handle for controlling movement of the flexible steering platform. In one embodiment, the flexible steering platform can include a plurality of axially aligned links and a plurality of flexible connector elements. Adjacent links can be connected using at least two of the connector elements such that flexing one or more connector elements can bend the steering platform in one or more directions. Bending of the steering platform can be achieved using, for example, two or more cables that extend between the handle and the steering platform and through the links and the connecting elements such that movement of the handle can apply a force to one or more of the cables to cause the steering platform to bend in at least two directions. Such a range of motion can allow the steering platform to be more easily directed through the body. In an exemplary embodiment, the surgical device includes one or a plurality of cables configured to allow the steering platform to bend in one or more directions. In one embodiment, at least four cables configured to allow the steering platform to bend in at least four directions and in at least two planes of motion. The surgical device's shaft can be configured to receive a flexible surgical instrument therein such that a working end of the surgical instrument can be received within the steering platform, thereby allowing movement, e.g., steering, of the surgical instrument's working end to be controlled through movement of the steering platform. Such a configuration can be advantageous because any flexible surgical instrument can be used with the steering platform and be actively steered during a surgical procedure, even passively flexible surgical instruments. Additionally, the cables extending through the links and the connector elements can allow for increased free space within the interior of the device's working end, thereby allowing larger surgical instruments to be received therein. A person skilled in the art will appreciate that the particular configuration of the shaft and steering platform can vary and that the various control techniques described herein can be used with virtually any surgical instrument in which it is desirable to control movement of the surgical instrument's working end via movement of the steering platform.

A person skilled in the art will appreciate that while the methods and devices are described in connection with endoscopic procedures in which the surgical device is delivered through a natural orifice, the methods and devices disclosed herein can be used in numerous surgical procedures and with numerous surgical instruments. By way of non-limiting example, the devices can be used in laparoscopic procedures, in which the device is introduced percutaneously. The methods and devices can also be used in open surgical procedures. Furthermore, the surgical device can be configured to pass through any portion of a body, but in an exemplary embodiment, the surgical device is configured to pass through a tortuous pathway. A person skilled in the art will appreciate that the term "tortuous pathway" as used herein is intended to include a tubular body lumen or organ, e.g., the colon or esophagus. While the methods and devices disclosed herein are described in connection with steering a scoping device, e.g., an endoscope, a laparoscope, and a colonoscope, a person skilled in the art will also appreciate that the methods and devices disclosed herein can be used with any surgical instrument configured to be inserted into a body, such as through a natural orifice, through a puncture hole formed in tissue, and in any other way appreciated by a person skilled in the art. While the surgical instrument can be rigid and/or flexible, in an exemplary embodiment, at least a distal working end of the surgical instrument is flexible.

The devices discussed herein can be made from any combination of rigid and/or flexible materials, but in an exemplary embodiment the materials are biocompatible. A person skilled in the art will appreciate that the term "flexible" as used herein is intended to encompass a variety of configurations. Generally, a "flexible" member has some degree of elasticity, e.g., is capable of bending without breaking. In an exemplary embodiment, the device or at least portions thereof are composed of at least one biocompatible and flexible material, e.g., plastic, titanium, stainless steel, etc. Various portions of the device can also be formed from a shape memory material, such as Nitinol.

Figure 2:
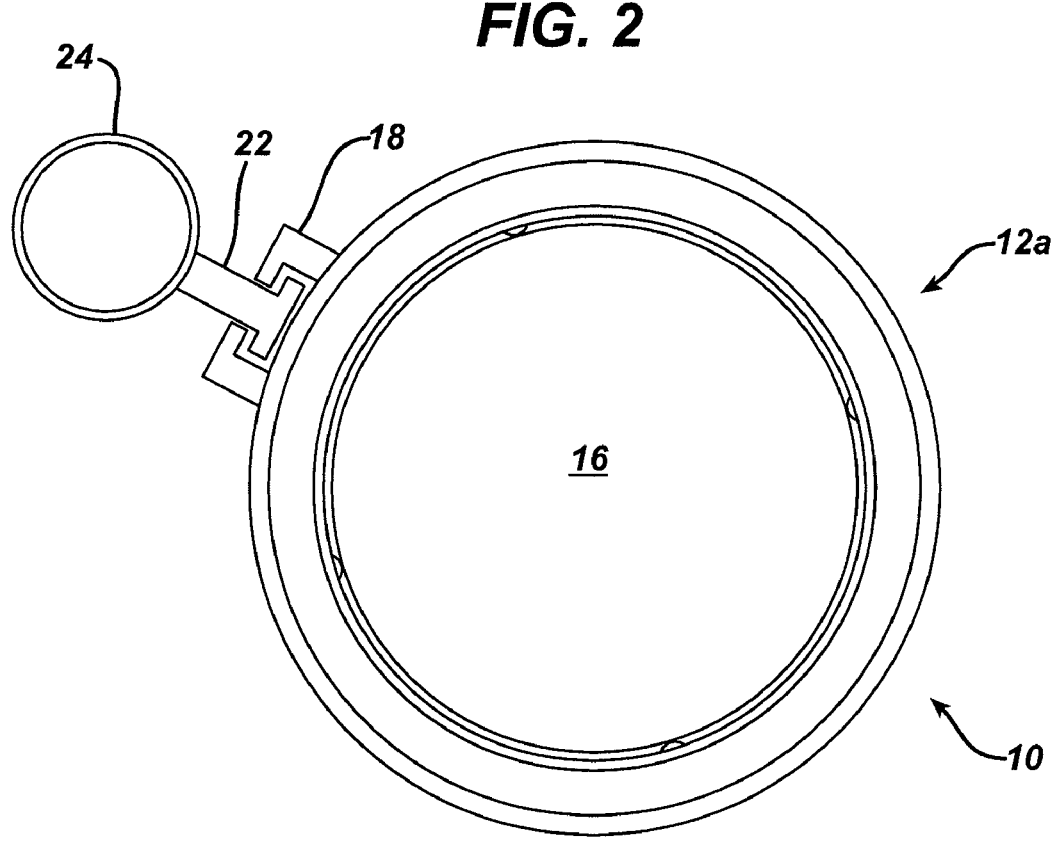
FIG. 2 is a proximal end view of the shaft of FIG. 1 with one embodiment of an accessory guide system mated thereto.

FIGS. 1 and 2 illustrate one exemplary embodiment of a flexible surgical device 10 effective for articulating a distal portion of a surgical instrument. Generally, the device 10 has a central passageway extending therethrough and includes an elongate shaft 12 and an articulating steering platform 14. The shaft 12 has an inner lumen 16 extending through the shaft 12 between proximal and distal ends 12a, 12b thereof that forms a portion of the device's central passageway, while the steering platform 14 has an inner lumen 20 extending between proximal and distal ends 14a, 14b of the steering platform 14 that is in communication with the shaft's inner lumen 16 and forms a remaining portion of the device's central passageway. The shaft's distal end 12b has the steering platform 14 coupled thereto or formed thereon, as will be discussed in more detail below. The steering platform 14 is configured to move in at least one direction using an actuator (not shown) that longitudinally extends along the device 10 between the shaft's proximal end 12a and a distal end 14b of the steering platform 14. In an exemplary embodiment, and as discussed further below, the actuator can include at least two cables spaced radially around a circumference of the device 10. Movement of a control mechanism at the shaft's proximal end 12a, e.g., a handle (not shown), can apply a force to one or more of the cables to cause at least one the cables to apply a force to the steering platform 14, thereby causing the steering platform 14 to move in at least one direction. In order to prevent the shaft 12 from flexing in response to force applied to the cables, the steering platform 14 can have a greater flexibility than the shaft 12. This can be achieved, for example, using the links and connector elements in the steering platform 14, and/or the shaft 12 can include a stabilizing element (not shown), such as a rod, extending therethrough to help make the shaft 12 more rigid than the steering platform 14.

The shaft 12 can have any size, shape, and configuration, as will be appreciated by a person skilled in the art. For example, the shaft 12 can be rigid, flexible, or a combination thereof, but in this illustrated embodiment it is flexible along a substantial longitudinal length thereof. As another example, the shaft 12 can be formed from a single component or multiple segments, and can be coiled or non-coiled. The flexibility of the shaft 12, as well as a relatively small diameter of its inner lumen 16, can allow the shaft 12 to be used in endoscopic procedures, whereby the device 10 is introduced translumenally through a natural orifice. In an exemplary embodiment, the shaft 12 can be substantially cylindrical, which can help ease the device's passage into and through the body and prevent the shaft 12 from harming or getting caught on tissue. The shaft 12 can have a uniform or non-uniform diameter along its longitudinal length. The shaft 12 can also vary in longitudinal length depending on the device's intended application.

The shaft's inner lumen 16 can be configured to receive a surgical instrument therein, as discussed further below. The inner lumen 16 can be a cannulated tunnel having any size and shape, but in an exemplary embodiment, the inner lumen 16 is substantially cylindrical and is sized to receive a surgical instrument such that the surgical instrument can be slidably movable therein. The inner lumen 16 can be located anywhere within the shaft 16 and can extend along the device's central longitudinal axis A, which is also the central longitudinal axis A of the shaft 12 and the steering platform 14.

The shaft 12 can optionally include an accessory guide system mated to the shaft 12 that is configured to facilitate introduction of surgical instruments into the body of a patient. A person skilled in the art will appreciate that a variety of techniques can be used to mate the accessory guide system either directly or indirectly to the device 10. In an exemplary embodiment, most clearly illustrated in FIG. 2, the guide system can include a track in the form of a rail 18 fixedly or removably coupled to the shaft 12 that extends longitudinally along an outside surface of the shaft 12, a mating member 22 configured to operatively couple to the rail 18, and an accessory channel 24 at a distal end of the mating member 22 that is configured as an elongate tubular member that can slidably receive and guide a surgical instrument therein external to and alongside the shaft 12. The accessory channel 24 and the shaft 12 have substantially equal longitudinal lengths such that a distal end of the accessory channel 24 is located proximal to the proximal end 14a of the steering platform 14 to avoid interference between the steering platform 14 and the accessory channel 24 when the steering platform 14 bends, but in some embodiments the accessory channel 24 can be longer or shorter than the shaft 12. A surgical instrument advanced through the accessory channel 24 can extend beyond the accessory channel's distal end and extend external to and alongside the steering platform 14 and/or beyond the steering platform's distal end 14b. However, in some embodiments, an end cap (not shown) can be attached to the accessory channel's distal end to help hold in place a distal end of a surgical instrument disposed within the accessory channel 24 to help prevent interference between the steering platform 14 and the surgical instrument. Non-limiting examples of an accessory guide system can be found in U.S. Patent Publication No. 2004/0230095 titled "Medical Apparatus For Use With An Endoscope" filed Nov. 18, 2004, which is hereby incorporated by reference in its entirety.

Figure 3:
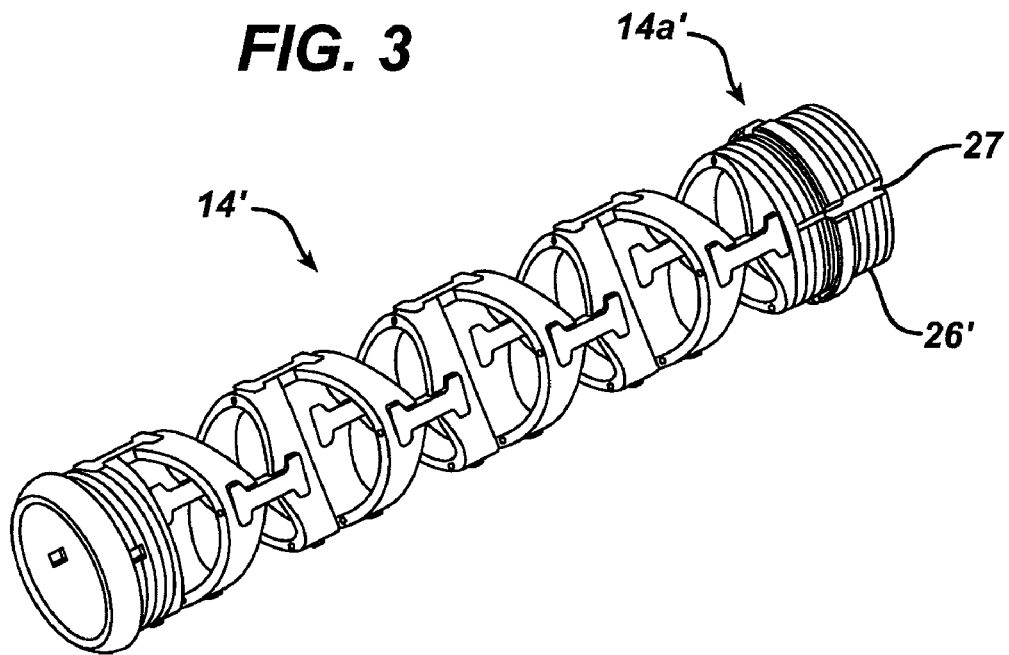
FIG. 3 is a perspective view of one embodiment of a removable steering platform.

The steering platform 14 can be fixedly coupled to the shaft 12 where the steering platform 14 is integrally formed with the shaft 12 such that the device 10 is a singular surgical tool, or the steering platform 14 can be removably coupled to the shaft 12. FIG. 3 illustrates an alternate embodiment of a steering platform 14' configured as an independent piece configured to be removably coupled to an elongate shaft (not shown) similar to the shaft 12 by connecting the steering platform's proximal end 14a' to the elongate shaft's distal end using a coupling mechanism. By using a removable steering platform, the surgical device can be fitted with an appropriately sized steering platform for a particular surgical procedure or a desired surgical instrument to be disposed therein. Furthermore, the surgical device can be provided as part of a kit including an elongate shaft and a plurality of different removable steering platforms, e.g., different longitudinal lengths, differently shaped inner lumen, composed of different materials having different degrees of flexibility, etc., that can be coupled to the elongate shaft as desired.

The coupling mechanism can permanently couple the removable steering platform 14' to the elongate shaft, or the steering platform 14' can be removable from the elongate shaft following its coupling thereto. In the illustrated embodiment, the coupling mechanism includes threads 26 formed on an outer surface of the steering platform's proximal end 14a' that are configured to mate with threads (not shown) on an inner surface of the distal end of the elongate shaft. A person skilled in the art will appreciate that any one or more coupling mechanisms can be used to removably couple the elongate shaft and the steering platform 14', such as corresponding threads, a snap fit using interlocking protrusions and indentations, an adhesive, etc. The threads 26 can be radially continuous around an outer surface of a proximal link 32p' at the steering platform's proximal end 14a' or, as illustrated in FIG. 3, the proximal link 32p' can include at least one longitudinal channel 27 distally extending from the proximal link's proximal side distally along at least a partial longitudinal length thereof such that the threads 26 are non-continuous. Each channel 27 can seat one of the actuating cables, discussed further below, used to steer the steering platform 14' and can thereby help prevent the cables from interfering with the coupling of the steering platform 14' to a shaft, which can also have at least one similar longitudinal channel in its corresponding threads. Furthermore, the illustrated removable steering platform 14' has the threads 26 on its outside surface and is received within the elongate shaft, but in other embodiments, the steering platform's threads can be on an inner surface thereof such that an elongate shaft is received within the steering platform.

Figure 4:
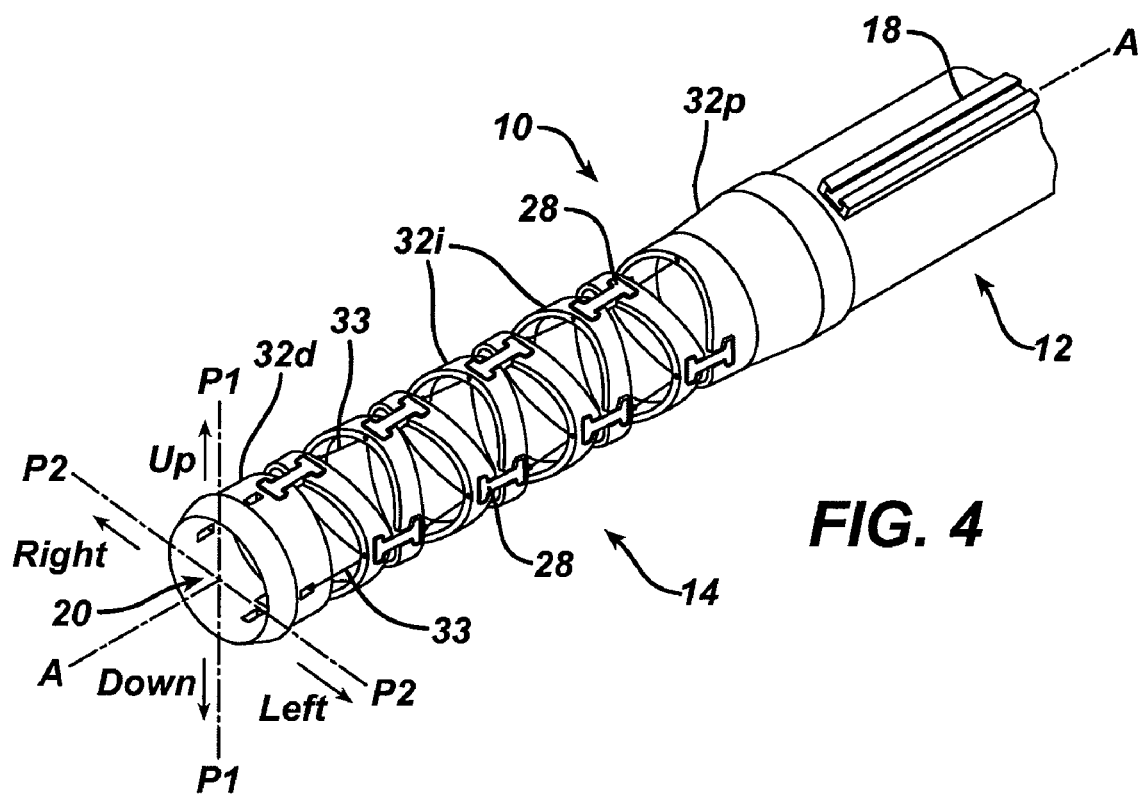
FIG. 4 is a perspective view of the distal end of the device of FIG. 1 including the steering platform and a portion of the shaft with the device in a resting position.

FIGS. 4 and 5 show an exemplary embodiment of the distal portion of the device 10, including the steering platform 14 attached to the distal end 12b of the shaft 12, in more detail. In order to facilitate steering of the steering platform 14, the steering platform 14 can include a plurality of links along a longitudinal length thereof with adjacent links being connected with one or more connector elements 28. The shape and size of the connector elements 28 and the links can vary, as discussed further below, but in this illustrated embodiment, the connector elements 28 and the links have sizes and shapes such that at least when the device 10 is in a resting position, e.g., at least when the steering platform 14 including its lumen 20 is substantially straight and unbent, adjacent links are separated by a minimum distance d. The minimum distance d can help provide adequate space for the links to move when the steering platform 14 is moved from its resting position. The steering platform 14 can have any longitudinal length, but in an exemplary embodiment, the steering platform 14 can have a longitudinal length that is in the range of about 10 to 25 mm and that is in a range of about 15% to 100% a longitudinal length of the shaft 12, e.g., about 25%. The steering platform's degree of curvature can vary, but in an exemplary embodiment, the steering platform 14 can bend up to about 180° in each direction of available motion, e.g., in each of the four available directions for the illustrated steering platform 14. The steering platform's radius of curvature can be controlled by the angle of deflection allowed between adjacent links. In one embodiment, to achieve a radius of curvature of about 6 cm, adjacent links with an outer diameter of about 18 mm can deflect an angle of about 15° relative to one another, although other angles between adjacent links can be possible depending on the desired radius of curvature. Angles between adjacent links in the range of about 5° to about 35° can produce varying radii of curvature. In some embodiments, the radius of curvature of the steering platform 14 can vary along the length of the steering platform 14 by varying angles of deflection between links along the length of the steering platform 14.

The links and the connector elements 28 can be flexible and/or rigid and can be formed from a variety of materials. In an exemplary embodiment, the links are substantially rigid, and the connector elements 28 are substantially flexible. In this way, the substantially rigid links can provide structural integrity to the steering platform 14 while the flexible connector elements 28 can allow for flexible steering of the steering platform 14 by flexing one or more of the connector elements 28 to bend the steering platform 14 and thus also a flexible surgical instrument received within the device 10. In an exemplary embodiment, the connector elements 28 are configured to be flexible in a side-to-side direction while resisting axial pulling, e.g., formed from a material such as polyurethane or any flexible elastomer.

Each of the connector elements 28 in the steering platform 14 can be identical, but one or more of the connector elements 28 can be different from any one or more other of the connector elements 28, e.g., be made from a different material, be larger, be smaller, have a differently sized lumen, etc. An exemplary embodiment of the connector element 28 is illustrated as a standalone element in FIG. 6. The connector element 28 has a symmetrical, dogbone shape with opposed cut-outs 28a in its sidewalls that define tabs 28b at the connector element's terminal ends 28c such that a width $w_t$ of the connector element 28 is greater at the tabs 28b than a width $w_m$ in a mid-portion 28e thereof. A height h of the connector element 28 can be substantially constant as shown to help provide adequate structural integrity to the connector element 28, although the height h can vary. Both tabs 28b can have the same shape and size as illustrated to help make the connector element 28 more universally attachable to any given link via either tab 28b, although the tabs 28b can have different sizes and shapes. A central longitudinal bore 28d extends axially through the connector element 28 between the connector element's terminal ends 28c. The central longitudinal bore 28d can have any shape, e.g., substantially cylindrical as shown, and can be configured to receive an actuation cable therein, as discussed further below. The central longitudinal bore 28d can also have any size, e.g., a diameter of about 0.028 inches (about 0.7112 mm). In an exemplary embodiment, the connector element 28 can have a height h of about 1.25 mm, a terminal end width $w_t$ of about 4 mm, a mid-portion width $w_m$ of about 2 mm, a longitudinal length of the mid-portion 28e of about 3.25 mm, a longitudinal length of the tabs 28b of about 1.5 mm.

The steering platform's links can be axially aligned such that central bores of each of the links are aligned to define the inner lumen 20 extending through the steering platform 14. As mentioned above, the inner lumen 20 is in communication with the inner lumen 16 of the shaft 12 and can similarly have any size and shape, but as shown in this embodiment it is substantially cylindrical. The inner lumens 16, 20 can have substantially the same diameter to form a central passageway of the device 10 having a substantially constant diameter to facilitate smooth slidable movement of a surgical instrument therein. The diameters of the inner lumens 16, 20 can vary, but in an exemplary embodiment they are in a range of about 10 to 25 mm.

Any surgical instrument such as a grasper, a scoping device, a cutting instrument, etc. can be slidably received within the device's central passageway, and any surgical instrument, including a second scoping device, can be slidably received within the guide system (if the guide system is present). In the exemplary embodiment illustrated in FIG. 5, a scoping device such as an endoscope 30 can be inserted in the device 10 through the proximal end 12a of the shaft 12 and moved through the device's central passageway to position a distal portion of the endoscope 30 within the steering platform 14. Movement of the steering platform 14 can thereby translate movement to the distal portion of the endoscope 30. A person skilled in the art will appreciate that the term "grasper" as used herein is intended to encompass any surgical instrument that is configured to grab and/or attach to tissue and thereby manipulate the tissue, e.g., forceps, retractors, movable jaws, magnets, adhesives, stay sutures, etc. A person skilled in the art will also appreciate that the term "cutting instrument" as used herein is intended to encompass any surgical instrument that is configured to cut tissue, e.g., a scalpel, a harmonic scalpel, a blunt dissector, a cautery tool configured to cut tissue, scissors, an endoscopic linear cutter, a surgical stapler, etc.

Figure 9:
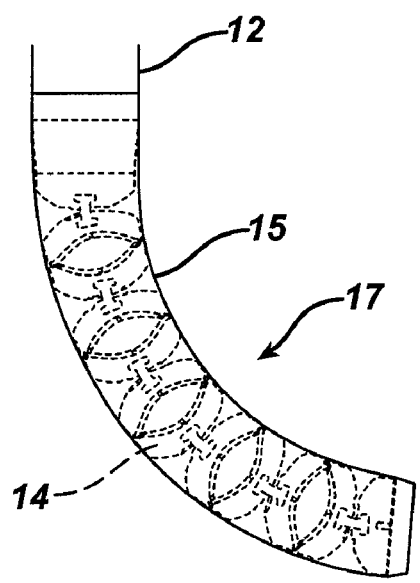
FIG. 9 is a perspective partially transparent view of the device of FIG. 1 with one embodiment of a sheath disposed over the steering platform.

Optionally, as illustrated in FIG. 9, an outer sheath 15 can be fixedly or removably disposed over the steering platform 14, collectively forming a steering segment 17. Generally, the sheath 15 can be configured to form a barrier between an external environment and the steering platform 14 to help protect the steering platform 14 from fluid and/or other debris that could damage or interfere with proper functioning of the steering platform 14 and/or a surgical instrument disposed therein. The sheath 15 is shown disposed over the steering platform 14, although the sheath 15 can additionally be disposed over at least a portion of the shaft 12. Non-limiting examples of a sheath can be found in U.S. patent application Ser. No. 12/111,425 titled "Methods and Devices for Maintaining Visibility" filed Apr. 29, 2008, which is hereby incorporated by reference in its entirety.

As will be appreciated by a person skilled in the art, the sheath 15 can have a variety of shapes, sizes and configurations. The sheath 15 can be formed from a variety of materials, e.g., C-Flex® available from Consolidated Polymer Technologies of Clearwater, Fla., and can be formed from a fluid impermeable, biocompatible material. The sheath 15 can be optically clear, translucent, opaque, or any combination thereof. An optically clear sheath can minimize obstruction of the viewing path of a scoping device received in the steering platform 14. If optically clear, the sheath can be formed from non-magnifying 1× material so as to be substantially non-modifying of the view provided by a scoping device disposed therein.

The sheath 15 can have any shape. In this illustrated embodiment, the sheath 15 has an elongate tubular shape having an open proximal end, a closed distal end, and an inner pathway extending longitudinally between its proximal and distal ends. The sheath 15 can be disposed around and receive the steering platform 14 within its inner pathway such that the sheath's distal end can cover the steering platform's distal end 14b, and the sheath's proximal end can be secured between the shaft's distal end 12b and the steering platform's proximal end 14a so as to form a fluid-sealed barrier around the steering platform 14. The sheath 15 can also thus form a fluid-sealed barrier around at least the distal portion of the device 10. In some embodiments, the sheath 15 can be coupled to the device 10 using an attachment mechanism configured to engage the sheath 15, e.g., at the sheath's proximal end, such as a clip, a clamp, adhesive, a groove, a hook, or any other coupling mechanism appreciated by a person skilled in the art. The attachment mechanism can be located on the steering platform 14, the shaft 12, the device's handle, and/or on an introducer device used to introduce the device 10 into a body cavity.

The size of the sheath 15 can vary, and the sheath 15 can have a size and shape that can correspond with the size and shape of the steering platform 14 when the sheath 15 is disposed therearound (with or without stretching or flexing of the sheath 15). The sheath 15 can also have any thickness, e.g., 0.015 in. thick. In some embodiments, an internal sheath (not shown) can be disposed inside of the steering platform 14. The internal sheath can be flexible and can be made from any material, such as a braided nylon tube, expanded PTFE (polytetrafluoroethylene), or other flexible lubricious, thin-walled material.

The quantity and size of the links forming the steering platform 14 can vary to obtain a desired flexibility. In an exemplary embodiment, the steering platform 14 includes at least three links with at least one link in each of its distal portion 14d, proximal portion 14p, and intermediate portion 14i located between the distal and proximal portions 14d, 14p. Exemplary embodiments of links in each of the portions 14i, 14d, 14p of the steering platform 14 are shown in FIGS. 10-20 and are described in more detail below. Although the links illustrated herein are shown as rings that each define a substantially circular bore extending therethrough, a person skilled in the art will appreciate that a "ring" can include any shape that defines a bore extending therethrough having any shape same or different from the ring, e.g., substantially circular, substantially elliptical, substantially hexagonal, substantially rectangular, etc.

Generally, the steering platform 14 includes a plurality of linearly aligned links including at least one intermediate link 32i in the intermediate portion 14i with two or more intermediate links 32i being connected using at least one connector element 28, a distal end link 32d in the distal portion 14d connected to a distal one of the intermediate links 32i using at least one connector element 28, and a proximal base link 32p in the proximal portion 14p connected to a proximal one of the intermediate links 32i using at least one connector element 28. The illustrated steering platform 14 includes seven intermediate links 32i in its intermediate portion 14i connected together using a plurality of connector elements 28, although the steering platform 14 can include any number of intermediate links 32i. The steering platform 14 can be configured to bend by flexing one or more of the connector elements 28 connecting the links 32i, 32d, 32p, such as by actuating an actuation mechanism.

In an exemplary embodiment, the device 10 can include at least one cable as an actuating mechanism. As will be appreciated by a person skilled in the art, a cable can be formed from any one or more materials, e.g., an electroactive polymer material or artificial muscle, a shape memory material such as Nitinol, etc., with the cable in an exemplary embodiment being flexible and biocompatible. The cable and its associated control mechanism, e.g., a handle, can have a variety of configurations. Non-limiting examples of cables and handles, including cables and handles configured to allow movement of the device's distal end to mimic motion of the handle, can be found in U.S. Patent Publication No. 2007/0225562 titled "Articulating Endoscopic Accessory Channel" filed Mar. 23, 2006, which is hereby incorporated by reference in its entirety.

As mentioned above, in the illustrated exemplary embodiment, at least two actuating cables 33 can extend longitudinally through at least a portion of the steering platform 14 and at least a portion of the shaft 12, and can be configured to bend the steering platform 14 in at least two directions. The cables 33 can have any size, shape, and configuration, but in an exemplary embodiment they are each at least the same length as the device 10 and substantially cylindrical. Each actuating cable 33 corresponds to a direction of bendable movement, with the illustrated embodiment including four cable 33 corresponding to four directions of movement indicated by the directional arrows labeled "up," "down," "left," and "right" in FIG. 4. A person skilled in the art will appreciate that the "up," "down," "right," and "left" directions are relative to a position of the steering element 14. As will also be appreciated by a person skilled in the art, the number and location of the actuating cables 33 can vary, but in an exemplary embodiment they are spaced substantially equidistantly radially around a circumference of the steering platform 14 to maximize available directional movement of the steering platform 14. Thus, with four cables 33 as shown, the cables 33 are spaced about 90° apart around the perimeter or circumference of the steering platform 14. Depending on the number and arrangement of the cables 33, the steering platform 14 can move in one or more planes of motion. As shown, two cables 33 can provide for motion of the steering platform 14 "up" and "down" in a first plane P1 and the other two cables 33 can provide for motion of the steering platform 14 "left" and "right" in a second plane P2, with the two planes P1, P2 being substantially perpendicular to each other because of the cables' substantially equidistant 90° spacing around the steering platform 14. In other embodiments where two or more actuating cables are not spaced apart by 90° or a multiple thereof, each cable can allow the steering platform to articulate in a different plane of motion. More than one cable can be simultaneously actuated to simultaneously bend the steering platform in more than one plane of motion.

Figure 7:
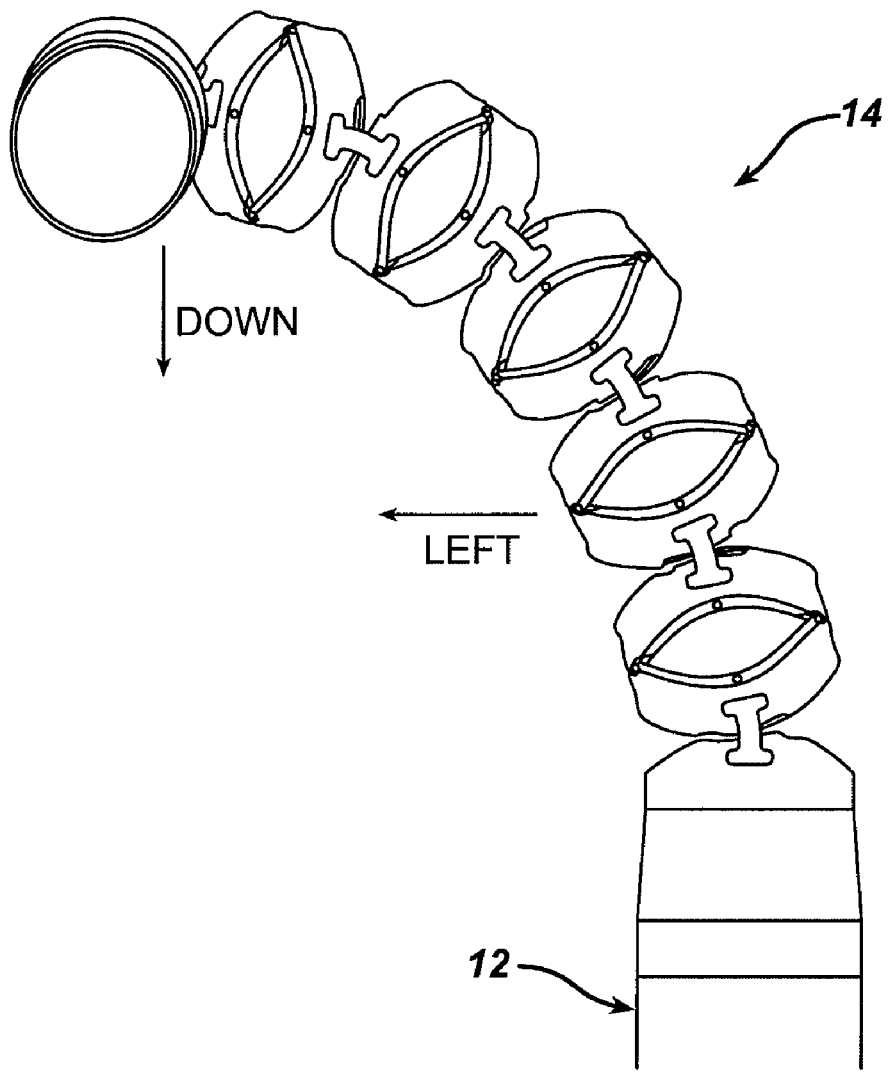
FIG. 7 is another perspective view of the distal end of the device of FIG. 1 including the steering platform and a portion of the shaft with the device bent in two planes of motion.

The cables 33 can engage the steering platform 14 in a variety of ways, but in an exemplary embodiment, each of the cables 33 pass through bores and/or channels in each of the links 32p, 32d, 32i and through bores in at least one of the connecting elements 28, as discussed further below. In this way, the cables 33 can be located outside the steering platform's inner lumen 20, thereby not obstructing inner lumen 20 for slidably receiving a surgical instrument therein, yet be protected within the steering platform 14 and limiting exposure of the cables 33 to an outside environment. Generally, an individual cable 33 can extend through one or more axially aligned connector elements 28 and the links 32p, 32d, 32i connected together by the one or more axially aligned connector elements 28. Because each connector element 28 connects two of the links, the total number of links and axially aligned connector elements 28 in the steering platform 14 has a two to one ratio, e.g., eight links to four connector elements 28 as shown in FIGS. 4 and 5. A distal end (not shown) of each of the cables 33 can attach to the distal link 32d in any way, as will be appreciated by a person skilled in the art, such as mechanical mating techniques, e.g., an adhesive, an interference fit, a ball-and-socket connection, threads, etc. A proximal end of the cables 33 can be coupled to a control mechanism at the shaft's proximal end 12a. In use, the connection of the cables 33 at the distal end of the distal link 32d can allow the cables 33 to apply a tension to the steering platform 14 when a force is applied to the cables 33 by manipulating the control mechanism. This tension can cause the steering platform 14 to flex in a direction dictated by the amount of tension applied to each cable 33. In this way, the steering platform 14 can be bent in at least one direction and up to as many directions as there are cables 33. Correspondingly, in the illustrated embodiment, the steering platform 14 can be bent in one of the planes P1, P2 or be simultaneously bent in both of the planes P1, P2. FIG. 7 shows one embodiment of the steering platform 14 being steered in two planes, bending "left" (toward the left side of the page) and "down" (out of the page).

Figure 8:
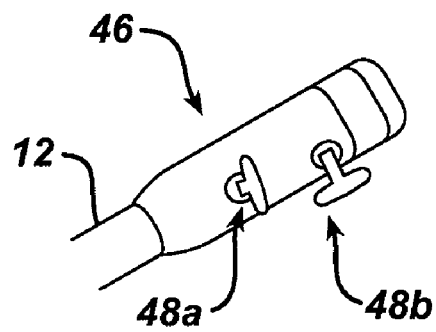
FIG. 8 is a perspective view of one embodiment of a handle attached to a proximal end of the shaft of FIG. 1.

An exemplary embodiment of a control mechanism in the form of a handle 46 is shown in FIG. 8. The handle 46 has first and second knobs 48a, 48b, each operatively connected to at least one of the cables 33. Manipulating the knobs 48a, 48b can actuate the cables 33, thereby bending the steering platform 14. In an exemplary embodiment, the first knob 48a is operatively connected to the two of the cables 33 configured to move the steering platform 14 in the first plane P1 and the second knob 48b is operatively connected to the two cables 33 configured to move the steering platform 14 in the second plane P2. Turning the first knob 48a in a first direction, e.g., clockwise, can move the steering platform 14 "up" in the first plane P1, while turning the first knob 48a in a second direction, e.g., counterclockwise, can move the steering platform 14 "down" in the first plane P1. Similarly, turning the second knob 48b in a first direction can move the steering platform 14 "right" in the second plane P2, while turning the second knob 48b in a second direction can move the steering platform 14 "left" in the second plane P2. A person skilled in the art will appreciate that the handle 46 can include any number of knobs or similar mechanism such as buttons or a joystick, that any of the first or second knobs 48a, 48b can control any of the cables 33, and that movement of the knobs 48a, 48b in any direction can be configured to bend the steering platform 14 in any direction as desired.

Figure 10:
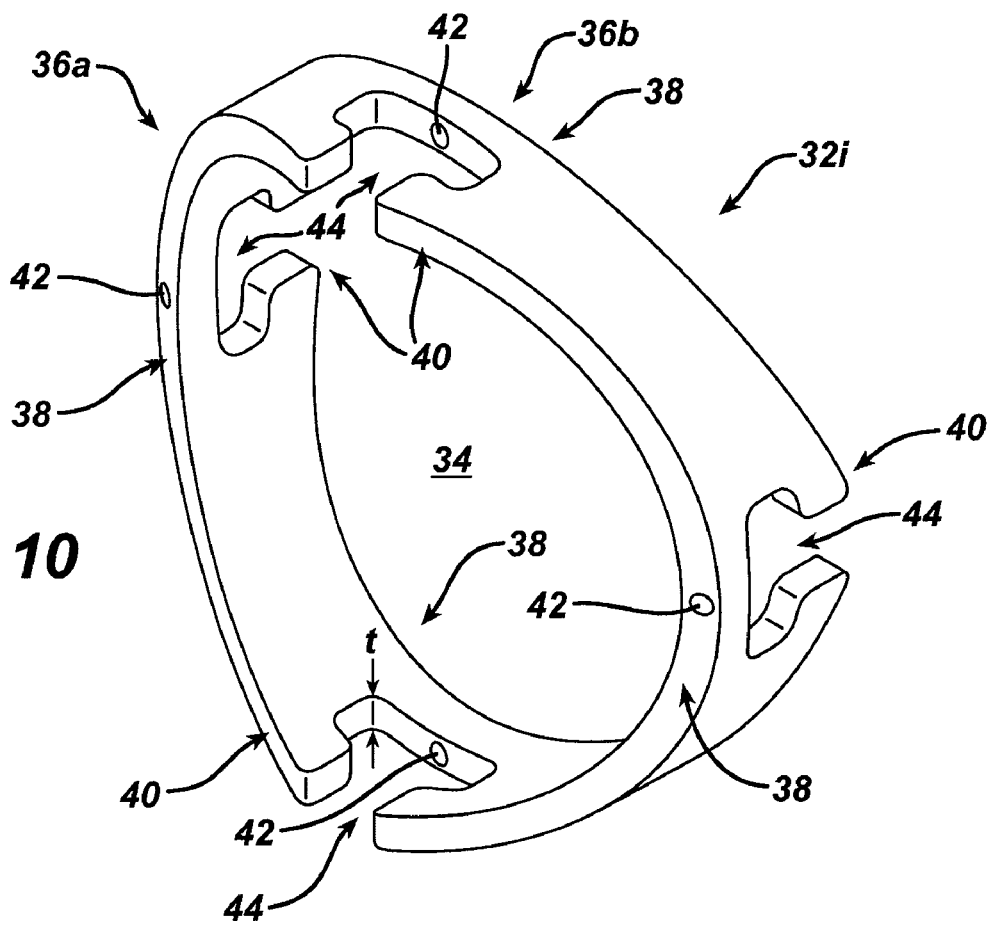
FIG. 10 is a perspective view of an intermediate link included in the steering platform of FIG. 1.
Figure 11:
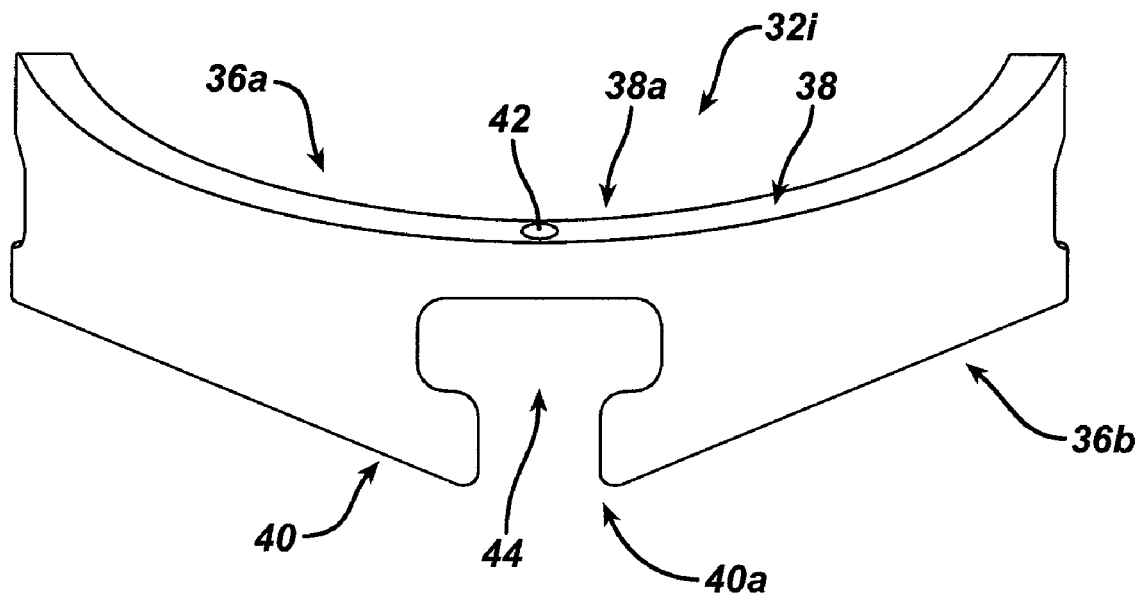
FIG. 11 is a side view of the intermediate link of FIG. 10.
Figure 12:
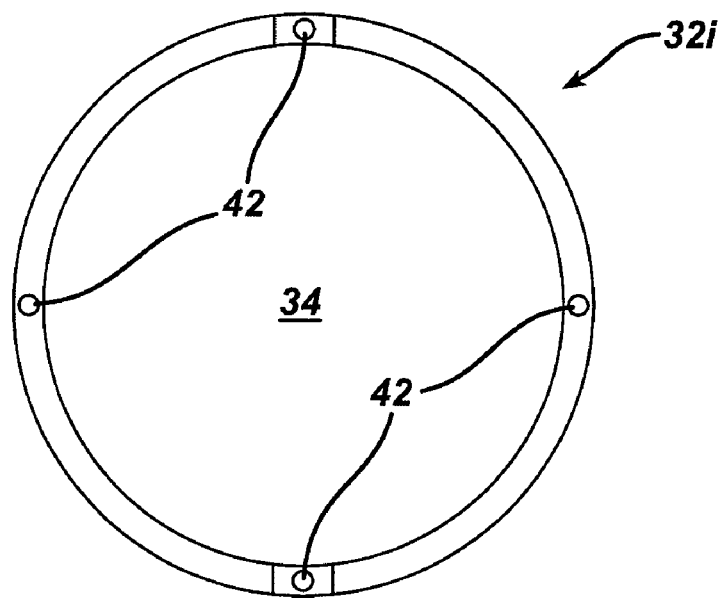
FIG. 12 is a proximal end view of the intermediate link of FIG. 10.
Figure 13:
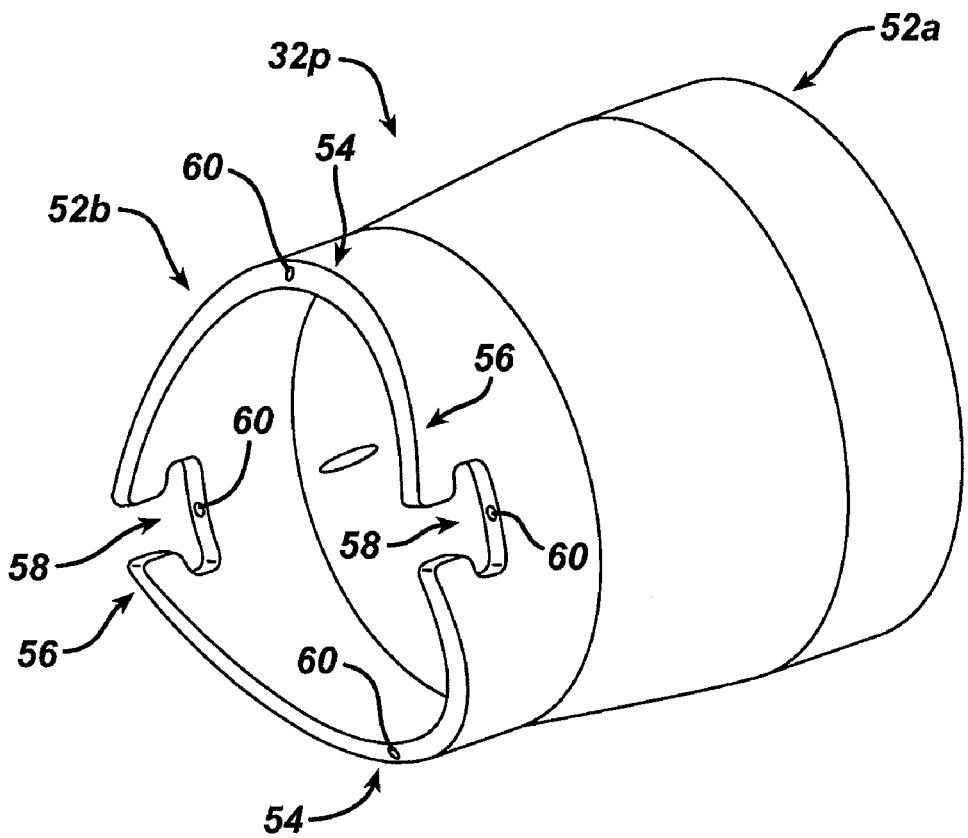
FIG. 13 is a perspective view of a proximal base link included in the steering platform of FIG. 1.

FIGS. 10-12 show one exemplary intermediate link 32i as a standalone element. The intermediate link 32i is a ring having a substantially circular hole 34 extending axially therethrough between proximal and distal sides 36a, 36b of the intermediate link 32i. The proximal and distal sides 36a, 36b are identified as such by example only as either side of the intermediate link 32i can be proximal or distal when the intermediate link 32i is linearly aligned with other links as assembled in the steering platform 14, as discussed further below.

Each of the intermediate link's proximal and distal sides 36a, 36b has at least two concave surfaces 38 and at least two convex surfaces 40. The concave and convex surfaces 38, 40 on a same side of the intermediate link 32i can alternate around the intermediate link 32i such that the perimeter surfaces on the proximal and distal sides 36a, 36b are each wave-like. The proximal and distal sides 36a, 36b can have complementary wave-like patterns such that a zenith point 38a of a concave surface 38 on the proximal side 36a is at a particular location around the circumference around the intermediate link 32i, while a nadir point 40a of a convex surface 40 is on the distal side 38a substantially at that particular location. In this way, the number of concave surfaces 38 on one of the intermediate link's proximal and distal sides 36a, 36b can equal the number of convex surfaces 40 on the other side of the intermediate link 32i, and vice versa. The concave and convex surfaces 38, 40 can each have any length along the perimeter surface of a side of the intermediate link 32i in any way, but in an exemplary embodiment the surfaces 38, 40 have equal lengths around the perimeter surface of a side to help equalize directional bending of the steering platform 14. In the illustrated exemplary embodiment, each side 36a, 36b of the intermediate link 32i has two opposed concave surfaces 38 separated from each other by about 180° and two opposed convex surfaces 40 separated from each other by about 180°, with adjacent concave and convex surfaces 38, 40 on a same side of the intermediate link 32i therefore being separated by about 90°. The degree of curvature of the concave and convex surfaces 38, 40 can vary, but in an exemplary embodiment, the concave and convex surfaces 38, 40 each have a radius of curvature in a range of about 10 to 15 mm (positive for convex surfaces and negative for concave surfaces), e.g., about 12 mm.

Each of the proximal and distal sides 36a, 36b has at least one recess 44 that is configured to couple to a connecting element 28. In this way, the intermediate link 32i can connect to two additional links via the at least two connecting elements 28, each connecting element 28 connected to one of the two additional links where one additional link is positioned adjacent to either side 36a, 36b of the intermediate link 32i such that the links are linearly aligned. Generally, each recess 44 corresponds to one direction of movement of the steering platform 14 in which the intermediate link 32i is included. As shown in this exemplary embodiment, the intermediate link 32i includes four recesses 44, two on each of the proximal and distal sides 36a, 36b, thereby corresponding to movement of the steering platform 14 in four directions. Each convex surface 40 can have a recess 44 formed therein substantially at its zenith point 40a, thereby allowing a connector element 28 to connect to each of the intermediate link's convex surfaces 40 and couple the intermediate link 32i to another one of the links in the steering platform 14. Thus, the recesses 44, like the convex surfaces 40 in this illustrated exemplary embodiment, can be spaced equidistantly radially around in the intermediate link 32i.

The recess 44 can have any size and shape to facilitate its coupling with a connecting element 28. As illustrated in this exemplary embodiment, the recesses 44 have shapes and sizes corresponding to the terminal ends 28c of the connecting element 28, e.g., to the tabs 28b and a portion of the mid-portion 28e, such that one of the connecting element's terminal ends 28c can be disposed in the recess 44 of the intermediate link 32i. As will be appreciated by a person skilled in the art, the connecting element 28 can be disposed in the recess 44 of the intermediate link 32i in any one or more ways, e.g., with an interference fit, with an adhesive, etc. In an exemplary embodiment, the connecting element 28 can be overmolded to a previously molded intermediate link 32i to provide a cost-effective, mass-producible, secure attachment between the connecting element 28 and the intermediate link 32i.

The intermediate link 32i has at least one bore 42 formed therein that extends between the proximal and distal sides 36a, 36b and that is configured to receive one of the actuating cables 33 therein. In the illustrated exemplary embodiment, the intermediate link 32$i$ has four bores 42 formed therein. Although the bores 42 can have any shape and size, the bores 42 as shown are substantially cylindrical to correspond to the shape of the cables 33. In the assembled steering platform 14, each bore 42 through the intermediate link 32$i$ axially aligns with a bore 28$d$ of a connector element 28 such that a single cable 33 can pass through both the intermediate link 32$i$ and one connector element 28 attached to the intermediate link 32$i$. The intermediate link's bores 42 thus can have a diameter substantially equal to a diameter of the bore 28$d$ in the connector element 28 to facilitate secure engagement of the cable 33 extending through at least one intermediate link 32$i$ and at least one connecting element 28. The bores 42 in the intermediate link 32$i$ and the bores 28$d$ in the connector elements 28 can be formed before or after the intermediate links 32$i$ and the connector elements 28 are coupled together.

Figure 14:
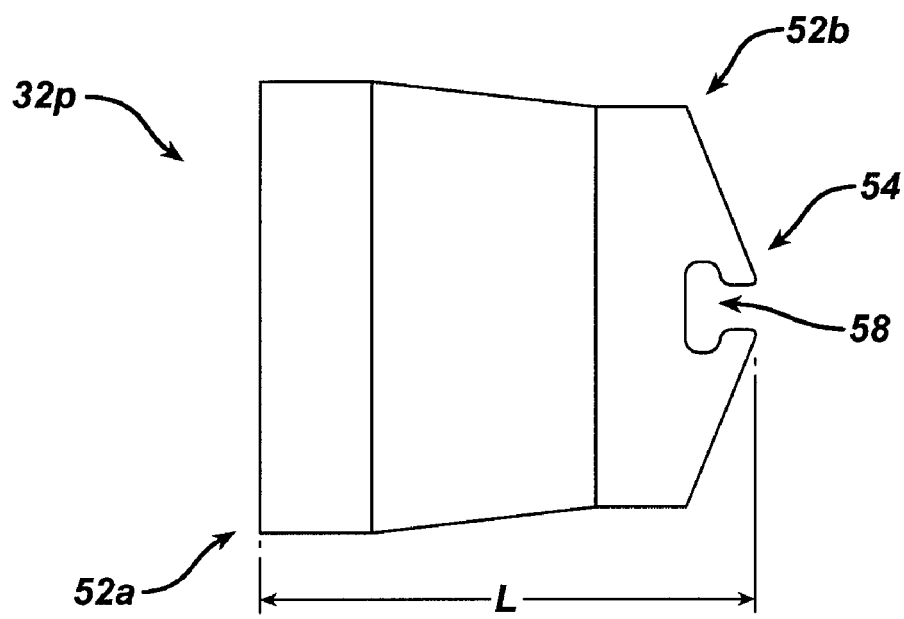
FIG. 14 is a side view of the proximal base link of FIG. 13.
Figure 15:
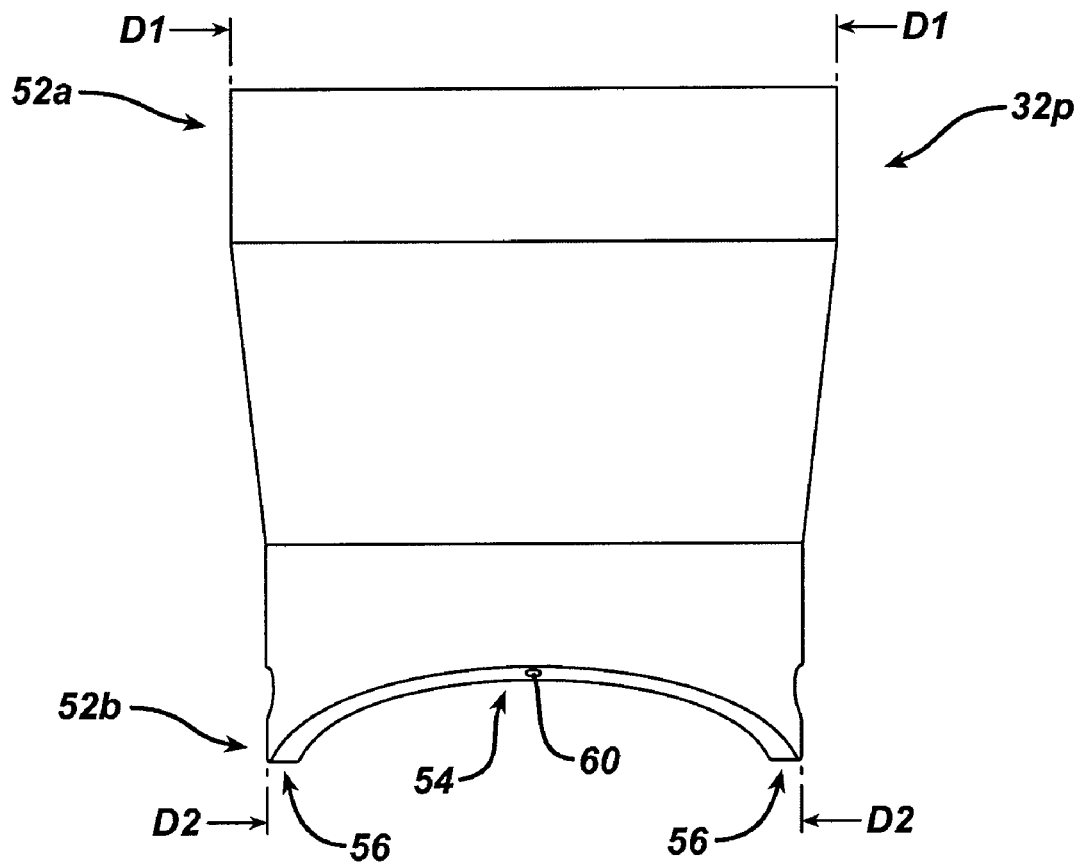
FIG. 15 is another side view of the proximal base link of FIG. 13.
Figure 16:
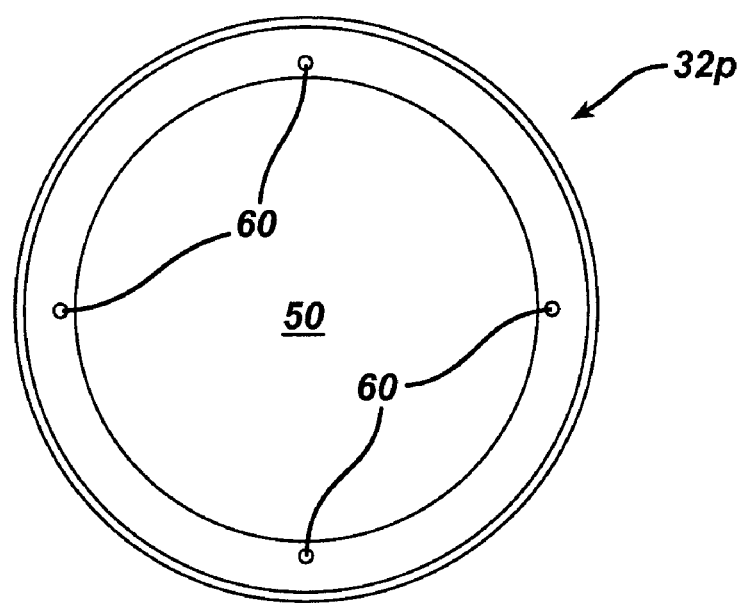
FIG. 16 is a distal end view of the proximal base link of FIG. 13.

FIGS. 13-16 show one exemplary proximal link 32$p$ as a standalone element. Similar to the intermediate link 32$i$, the proximal link 32$p$ is a ring having a substantially circular hole 50 extending axially therethrough between proximal and distal sides 52$a$, 52$b$ of the proximal link 32$p$. While the proximal link's hole 50 can have a substantially constant diameter to help receive a surgical instrument therein, an outer diameter of the proximal link 32$p$ can vary along the proximal link's longitudinal length L. As shown in FIGS. 14 and 15, the proximal link 32$p$ can distally taper such that a proximal diameter D1 at its proximal side 52$a$ is larger than a distal diameter D2 at its distal side 52$b$. Having a smaller distal diameter D2 can allow the steering platform 14 to be as small as possible and improve its maneuverability in the body of a patient. The proximal link 32$p$ can have any longitudinal length L, and its longitudinal length can be larger than a longitudinal length of an individual intermediate link 32$i$ and larger than a longitudinal length of the distal link 32$d$ to help facilitate a secure connection between the shaft 12 and the steering platform 14. Further, the proximal link 32$p$ can include one or more longitudinal channels, similar to the channels 27 discussed above, that distally extend from the proximal link's proximal side 52$a$ along at least a partial longitudinal length thereof and that can each seat a cable.

As also shown in FIGS. 14 and 15, the proximal link's proximal side 52$a$ can be substantially flat, which can also help facilitate a secure connection between the shaft 12 and the steering platform 14 as the shaft's distal end 12$b$ in this exemplary embodiment is also substantially flat. The proximal link's distal side 52$b$, however, can have at least two concave surfaces 54 and at least two convex surfaces 56, similar to the intermediate link's concave and convex surfaces 38, 40 described above such that the proximal link 32$p$ can have a wave-like surface on its distal side 52$b$. While the proximal link's concave and convex surfaces 54, 56 can have any size, shape, and configuration, in an exemplary embodiment they are identical to those on the intermediate link 32$i$ to facilitate coupling of the proximal link 32$p$ thereto. The proximal link 32$p$ can connect to a proximal-most one of the linearly arranged intermediate links 32$i$ using at least one of the connector elements 28 as described above. The distal side 52$b$ of the proximal link 32$p$ has at least one recess 58, similar to the intermediate link's recess 44, that is configured to couple to a connecting element 28. The proximal link 32$p$ can also have at least one bore 60 formed therein, similar to the intermediate link's bore 42, that is configured to receive one of the actuating cables 33 therein.

FIGS. 17-20 illustrate one exemplary distal link 32$d$ as a standalone elements. Similar to the intermediate link 32$i$ and the proximal link 32$p$, the distal link 32$d$ is a ring having a substantially circular hole 62 extending axially therethrough between proximal and distal sides 64$a$, 64$b$ of the distal link 32$d$. The distal link's hole 62 can have a substantially constant diameter to help receive a surgical instrument therein, whereas an outer diameter of the distal link 32$d$ can vary along the distal length's longitudinal length L2. Generally, the distal link 32$d$ can proximally taper toward the proximal side 64$a$ along a first partial longitudinal length L3 of its longitudinal length L2 and can distally taper toward its distal side 64$b$ along a remaining longitudinal length L4 of its longitudinal length L2. The portion of the distal link 32$d$ along the remaining longitudinal length L4 can form a distal lip 76 having a larger diameter than the portion of the distal link 32$d$ along the first partial longitudinal length L3, which along with the lip's distal tapering can help the distal link 32$d$, and hence the steering platform 14 and the device 10, more easily be introduced to and traversed through a body of a patient.

Figure 18:
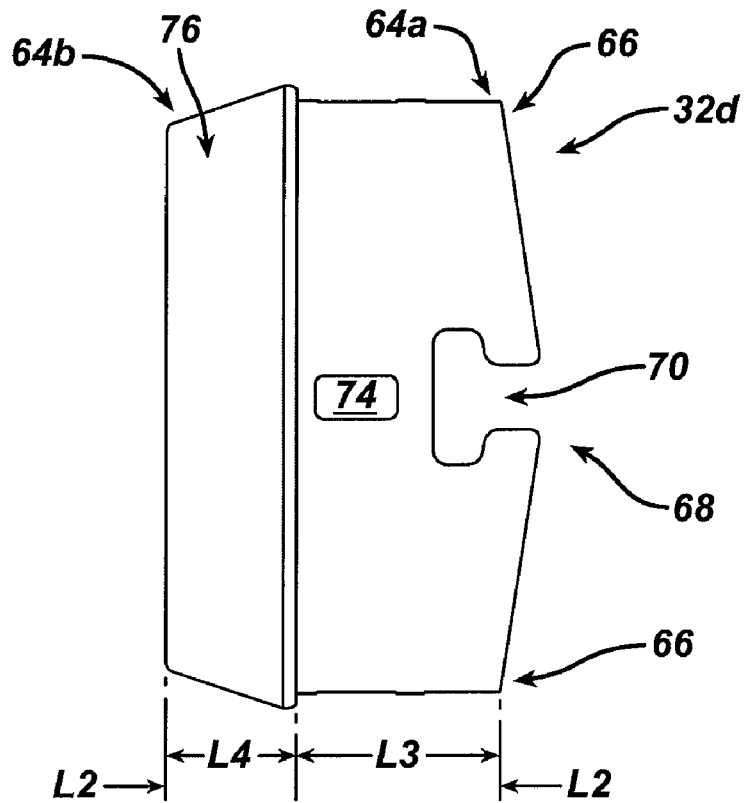
FIG. 18 is a side view of the distal end link of FIG. 17.

As shown in FIG. 18, the distal link's distal side 64$b$ can be substantially flat, which can help the steering platform 14 engage a surgical instrument disposed in its inner lumen 20 and minimize chance of the distal link 32$d$ interfering with use of the surgical instrument. The distal link's proximal side 64$a$, however, can have at least two concave surfaces 66 and at least two convex surfaces 68, similar to the intermediate link's concave and convex surfaces 38, 40 and the proximal link's concave and convex surfaces 54, 56 described above such that the distal link 32$d$ can have a wave-like surface on its proximal side 64$a$. While the distal link's concave and convex surfaces 66, 68 can have any size, shape, and configuration, in an exemplary embodiment they are identical to those on the intermediate link 32$i$ to facilitate coupling of the distal link 32$d$ thereto. The distal link 32$d$ can connect to a distal-most one of the linearly arranged intermediate links 32$i$ using at least one of the connector elements 28 as described above.

Figure 17:
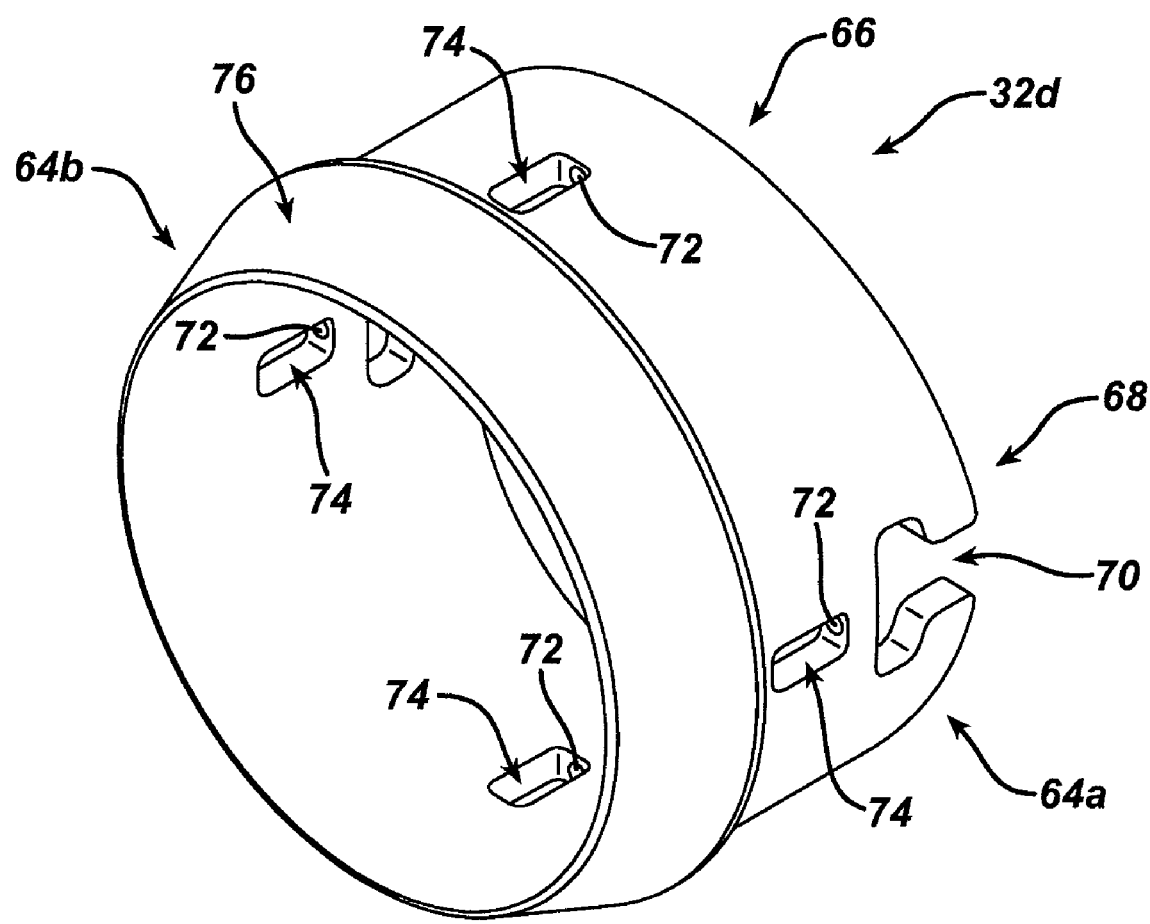
FIG. 17 is a perspective view of a distal end link included in the steering platform of FIG. 1.
Figure 19:
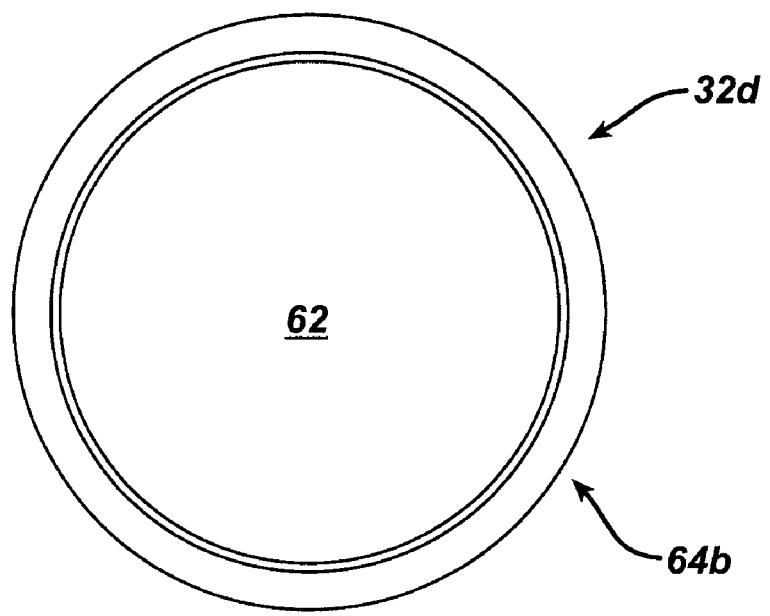
FIG. 19 is a distal end view of the distal end link of FIG. 17.
Figure 20:
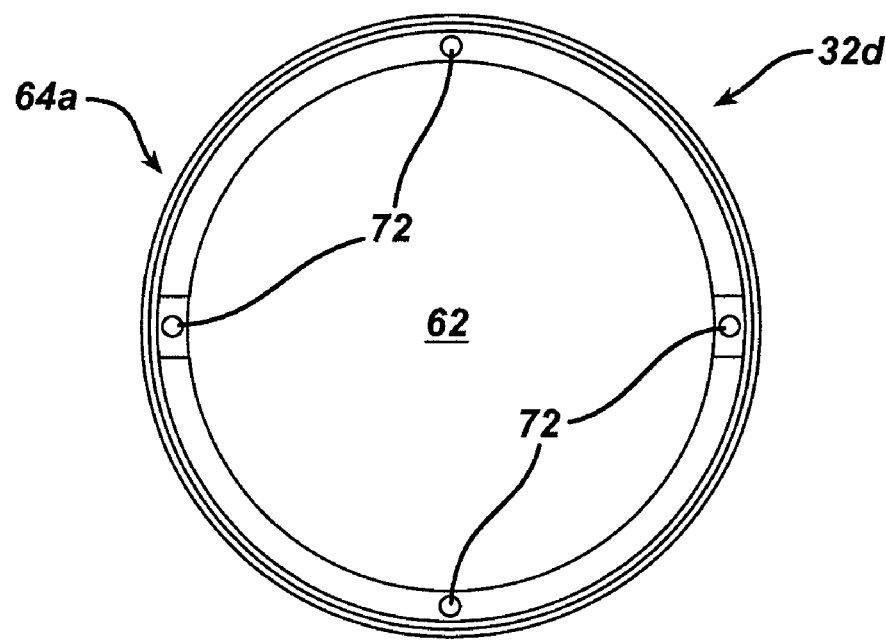
FIG. 20 is a proximal end view of the distal end link of FIG. 17.

Also similar to the intermediate link 32$i$ and the proximal link 32$p$, the distal link 32$d$ can have at least one recess 70, similar to the intermediate link's recess 44 and the proximal link's recess 58, that is configured to couple to a connecting element 28 and has at least one bore 72 formed therein, similar to the intermediate link's bore 42 and the proximal link's bore 60, that is configured to receive one of the actuating cables 33 therein. However, the one or more bores 72 formed in the distal link 32$d$ can extend only a partial length therethrough by extending distally from the distal link's proximal side 64$a$ such that the one or more bores 72 do not penetrate through the distal side 64$b$, as seen in FIGS. 17, 19, and 20. Such partial extension of the one or more bores 72 can help secure cables 33 disposed in the one or more bores 72 to the distal link 32$d$. Each bore 72 formed in the distal link 32$d$ can extend along any full or partial longitudinal length of the distal link 32$d$, with each bore 72 in an exemplary embodiment extending between the distal link's proximal side 64$a$ and an opening 74 formed in a sidewall of the distal link 32$d$. Each of the one or more openings 74 can be configured to facilitate securing distal ends of each of the cables 33 extending through the distal link's one or more bores 72, e.g., by providing adequate space for mechanical mating of the cables 33 to the distal link 32$d$ such as by being large enough to retain a ball or other retaining member formed on the end of each cable 33. The one or more openings 74 can each have any size, such as a size that is effective to retain a cable 33 therein. While the distal link 32$d$ can include any number of openings 74 at any location, the distal link 32$d$ in an exemplary embodiment has the openings 46 spaced equidistantly radially around the circumference of the distal link 32$d$ and a number of sidewall openings 74 equal to a number of recesses 70 and a number of bores 72 formed in the distal link 32d. While the openings 74 are illustrated as extending between inner and outer surfaces of the distal link 32d, the openings 74 can be cavities formed within the distal link 32d such that they are not visible through the distal link's sidewall (unless the sidewall is translucent or transparent).

The concave and convex surfaces of adjacent ones of the links 32i, 32p, 32d have a particular configuration when they are linearly aligned and connected together as in the steering platform 14. As shown in FIGS. 4 and 5, adjacent links can be axially positioned such that their concave surfaces face each other while their convex surfaces face each other. In this way, when the steering platform 14 bends, the concave surfaces of adjacent links are configured to move toward one another, thereby allowing for a greater degree of curvature of the steering platform 14 because the links have room to move as the steering platform 14 bends. In other words, the at least two opposed convex surfaces on the proximal sides of the distal link 32d and the one or more intermediate links 32i face the at least two opposed convex surfaces on the distal side of an adjacent link, while the at least two opposed concave surfaces on the proximal side of the distal link 32d and the one or more intermediate links 32i similarly face the at least two opposed concave surfaces on the distal side of an adjacent link.

Further, the connecting element 28 and the recesses 44, 58, 70 in each of the respective intermediate, proximal and distal links 32i, 32p, 32d can be sized such that the height h of the connecting element 28 is equal to or less than a thickness of a recess, e.g., a thickness t of the intermediate link's recess 44 as shown in FIG. 10. In this way, disposal of a connecting element 28 within the recesses of two adjacent links can position outside surfaces of the connecting element 28 flush with or within the two adjacent links. An outer diameter of the steering platform 14 can thus be defined by an outer diameter of the links 32i, 32p, 32d with a plurality of connector elements 28 connecting adjacent links because the connector elements 28 connecting the various links 32i, 32p, 32d do not protrude therefrom. Such a configuration can help maximize the diameter of the steering platform's inner lumen 20 for receiving surgical instruments while helping to minimize an outer diameter of the steering platform 14 to facilitate the device's 10 use in a minimally invasive surgical procedure.

Figure 21:
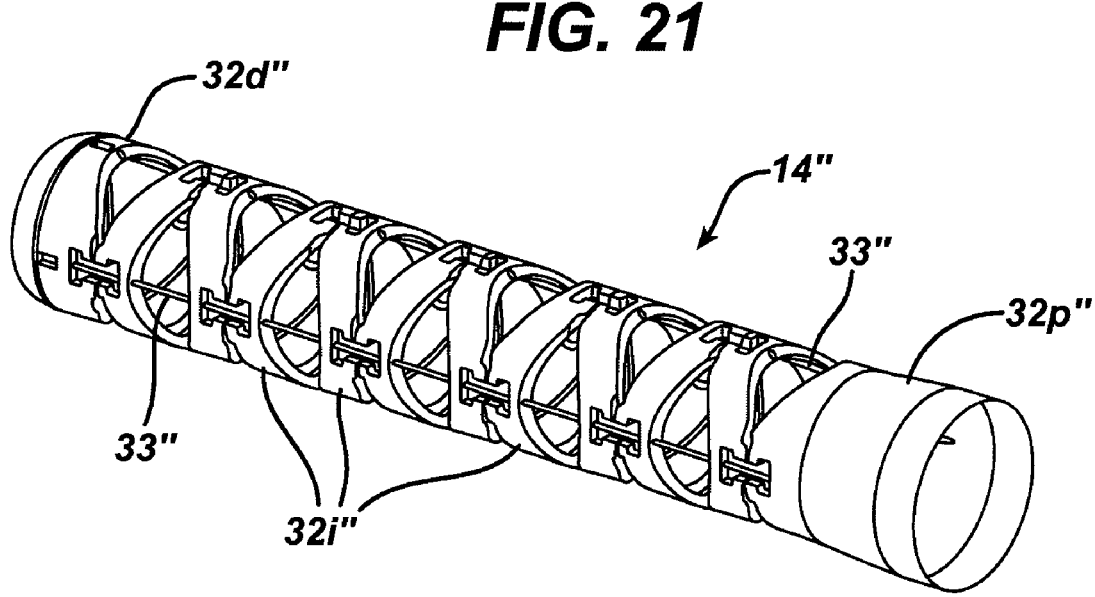
FIG. 21 is a perspective view of another embodiment of a steering platform in a resting position.
Figure 22:
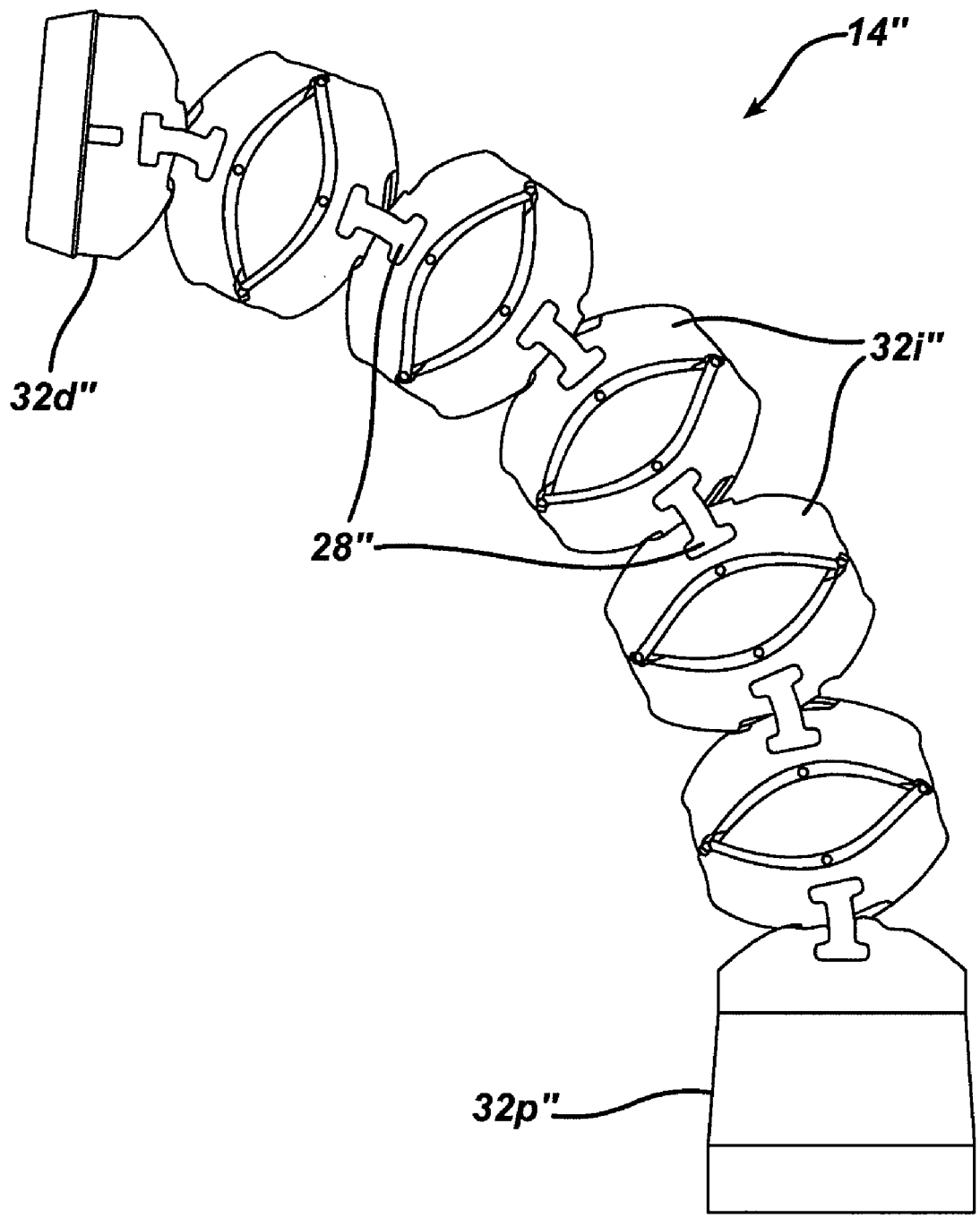
FIG. 22 is a side view of the steering platform of FIG. 21 in a bent position.
Figure 23:
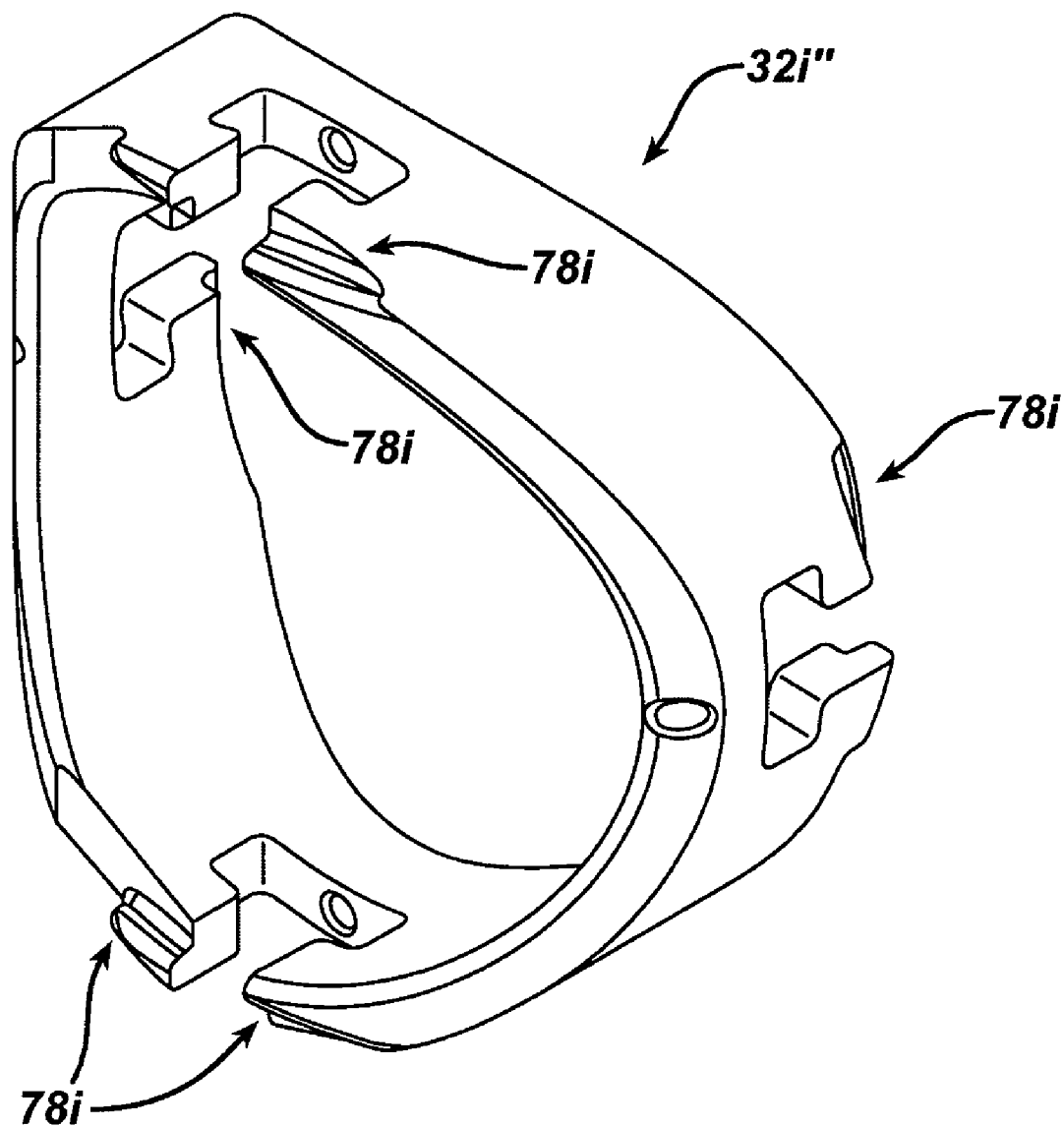
FIG. 23 is a perspective view of an intermediate link included in the steering platform of FIG. 21.
Figure 24:
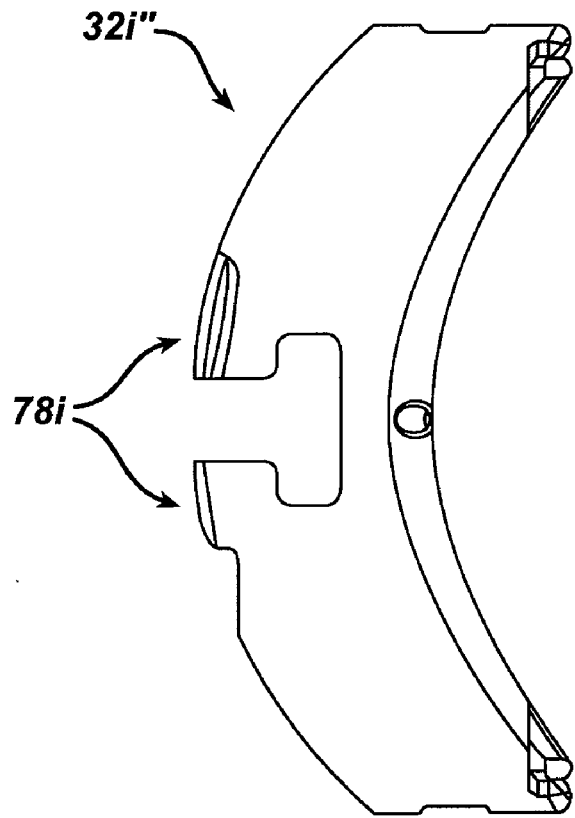
FIG. 24 is a side view of the intermediate link of FIG. 23.
Figure 25:
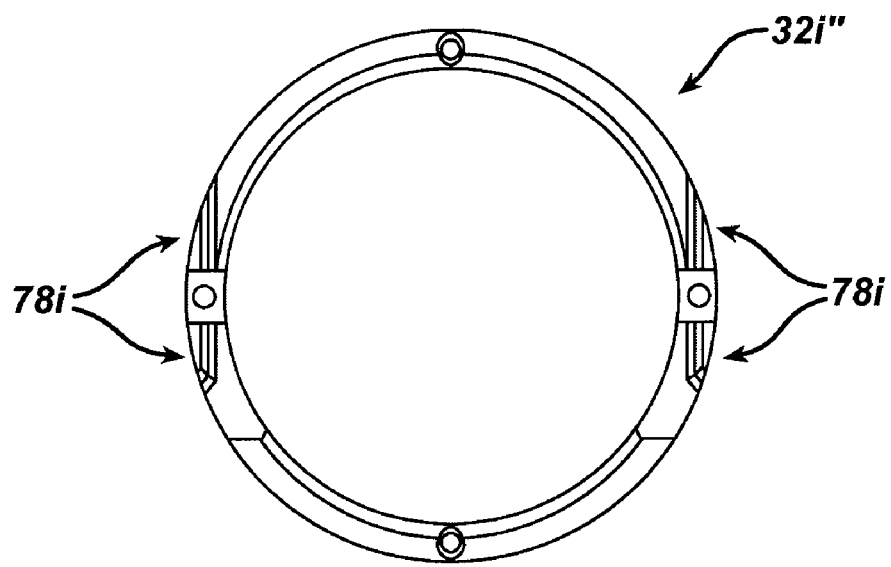
FIG. 25 is a distal end view of the intermediate link of FIG. 23.
Figure 26:
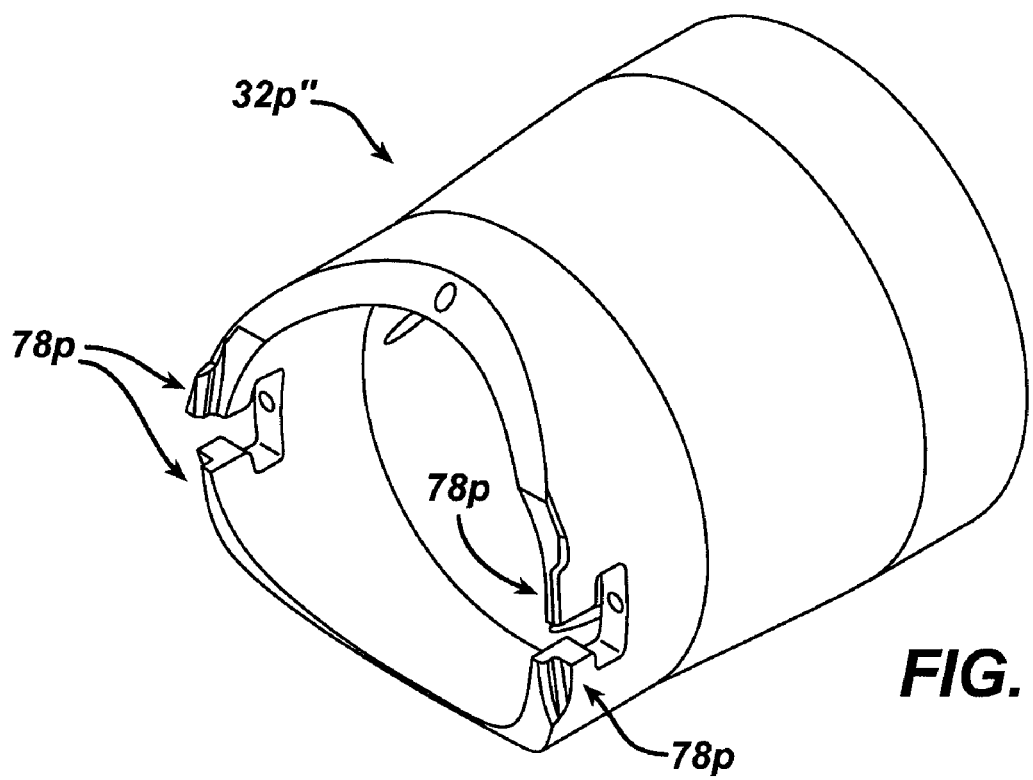
FIG. 26 is a perspective view of a proximal base link included in the steering platform of FIG. 21.
Figure 27:
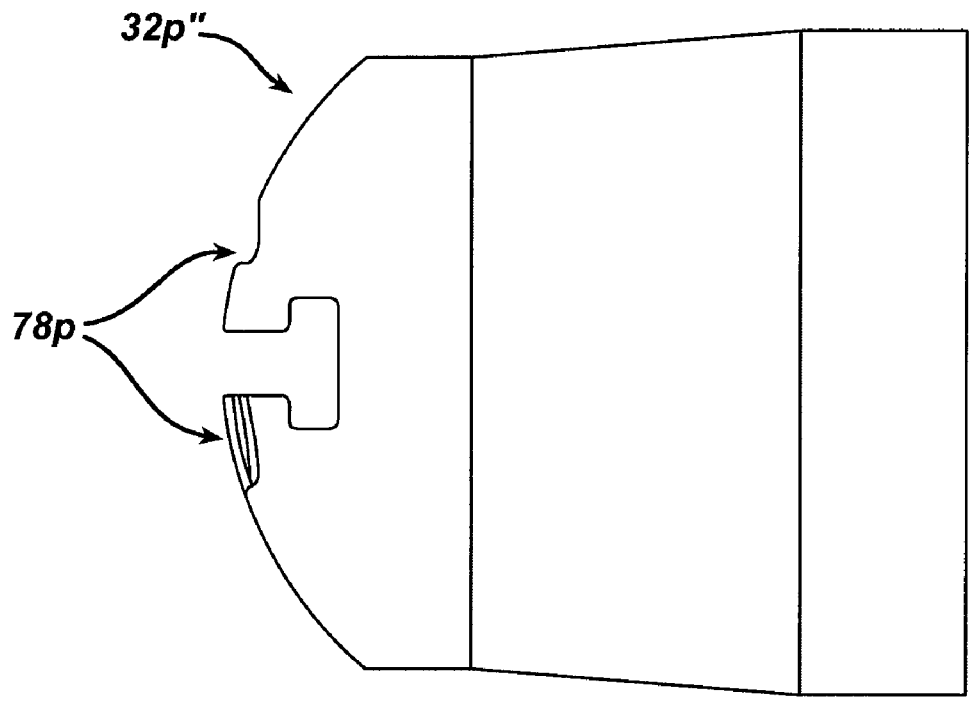
FIG. 27 is a side view of the proximal base link of FIG. 26.
Figure 28:
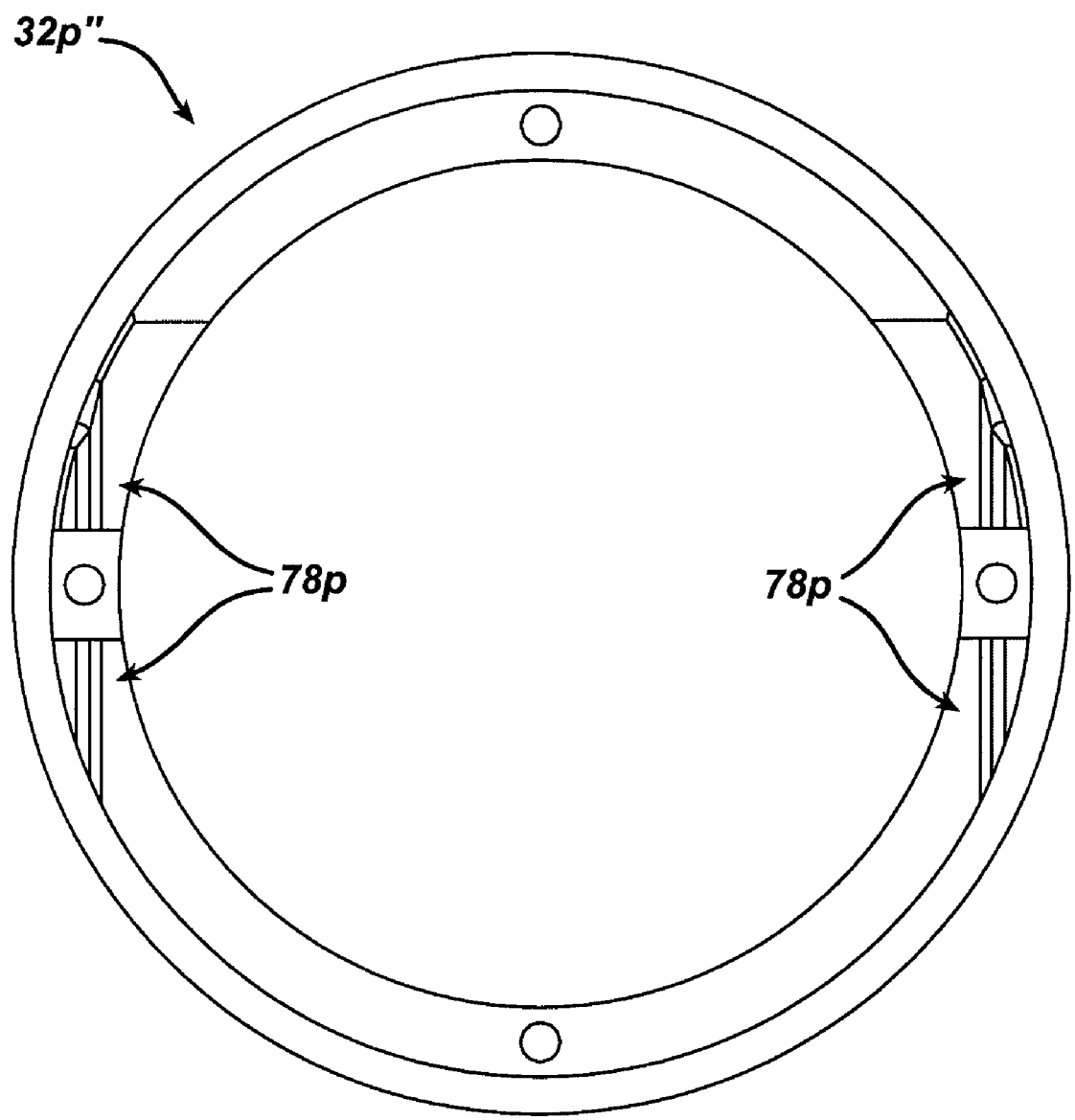
FIG. 28 is a distal end view of the proximal base link of FIG. 26.
Figure 29:
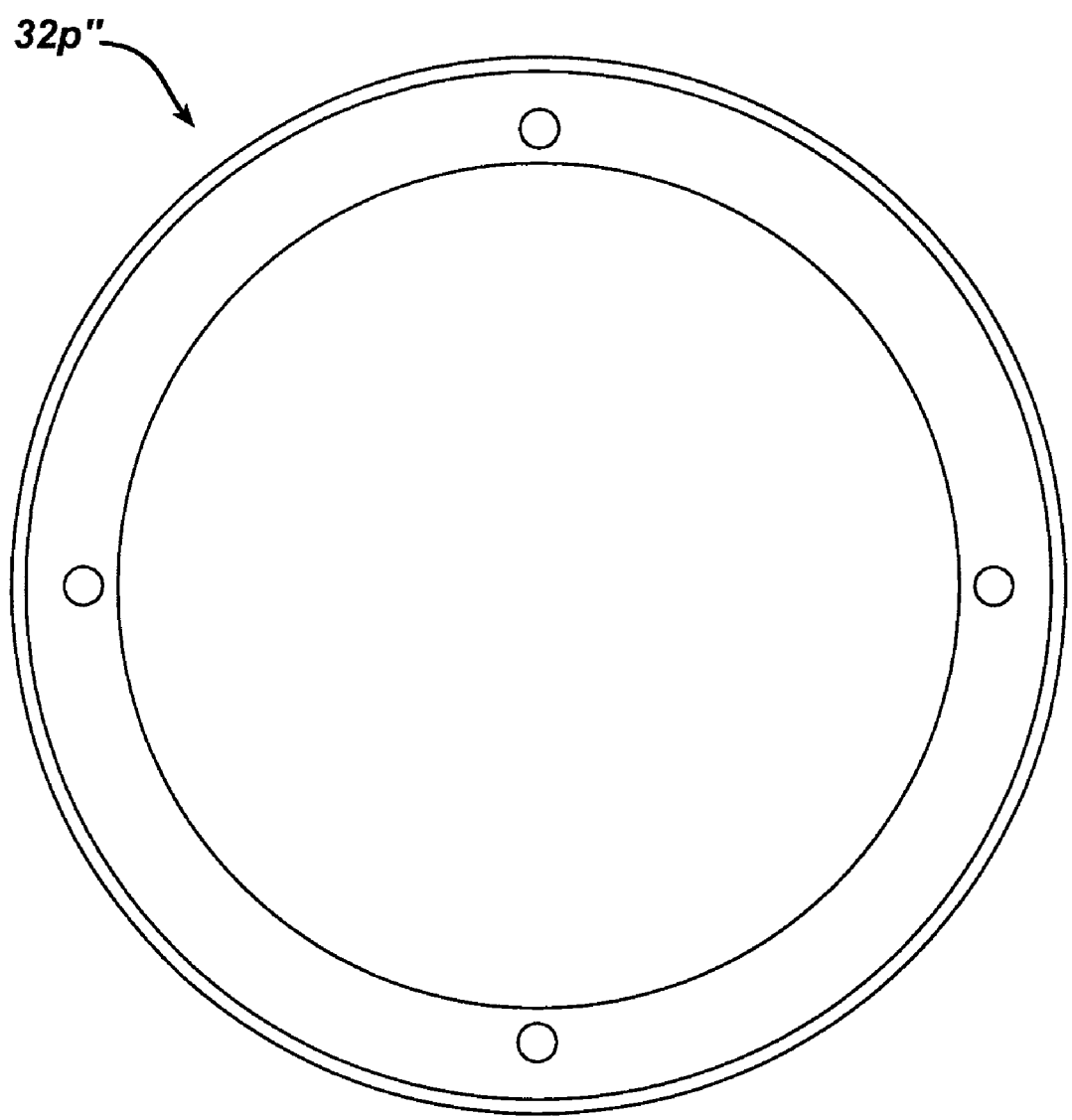
FIG. 29 is a proximal end view of the proximal base link of FIG. 26.
Figure 30:
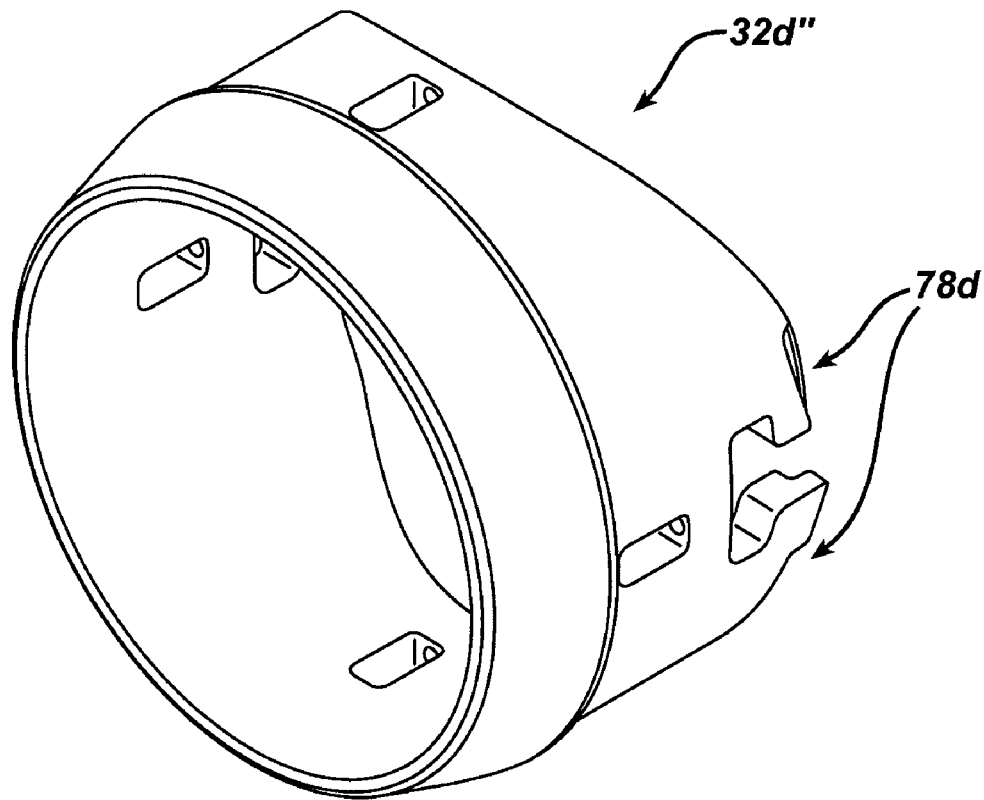
FIG. 30 is a perspective view of a distal end link included in the steering platform of FIG. 21.
Figure 31:
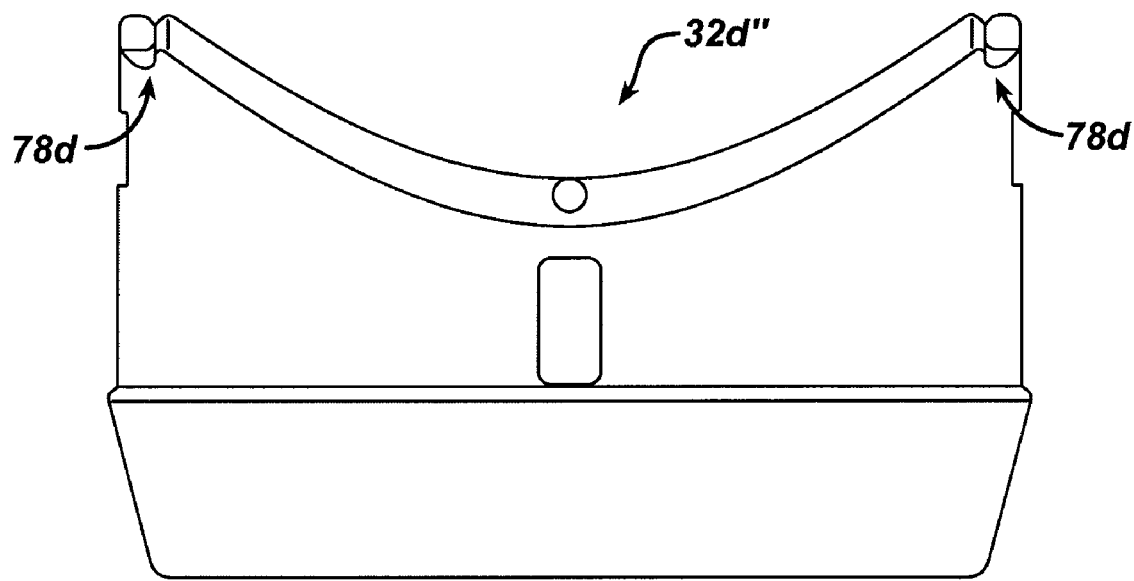
FIG. 31 is a side view of the distal end link of FIG. 30.
Figure 32:
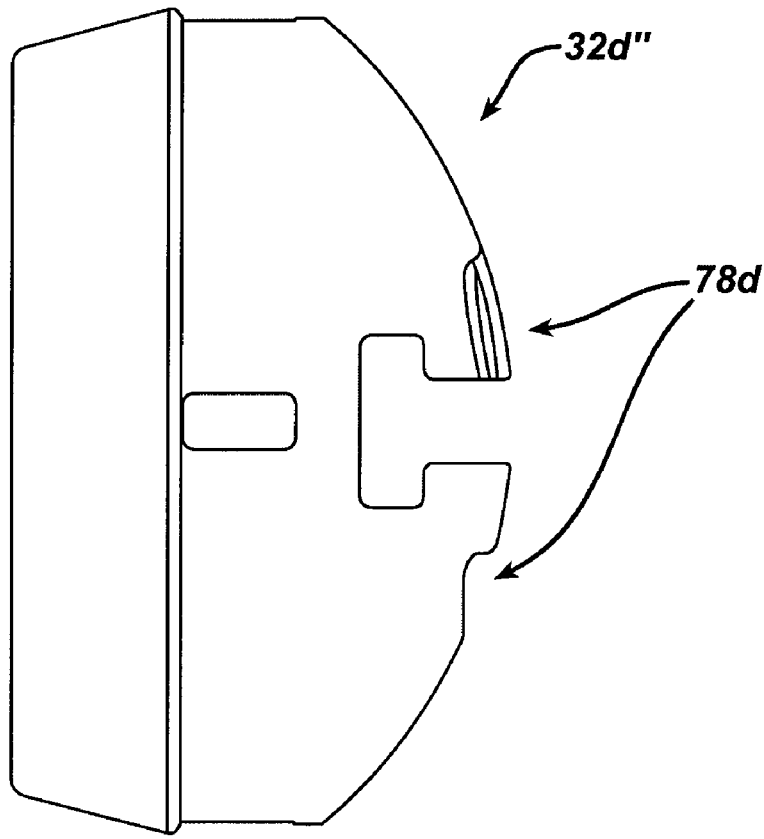
FIG. 32 is another side view of the distal end link of FIG. 30.
Figure 33:
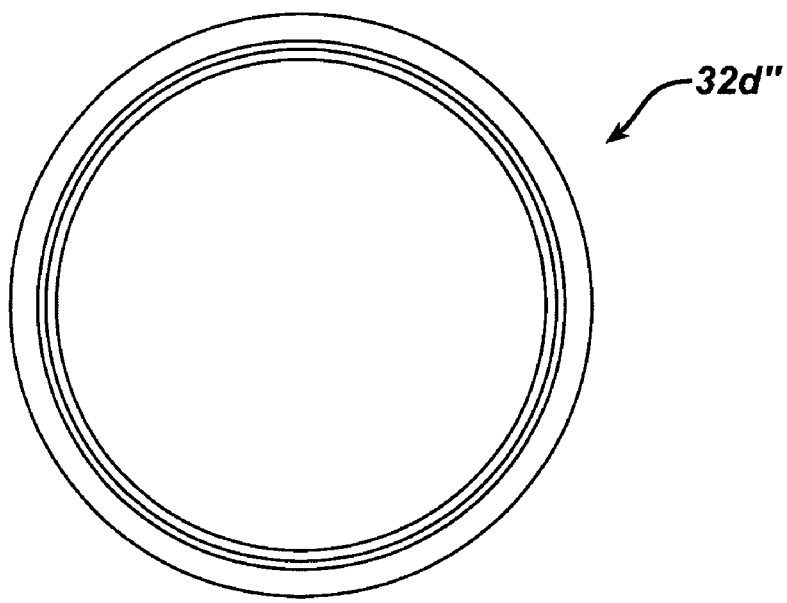
FIG. 33 is a distal end view of the distal end link of FIG. 30.
Figure 34:
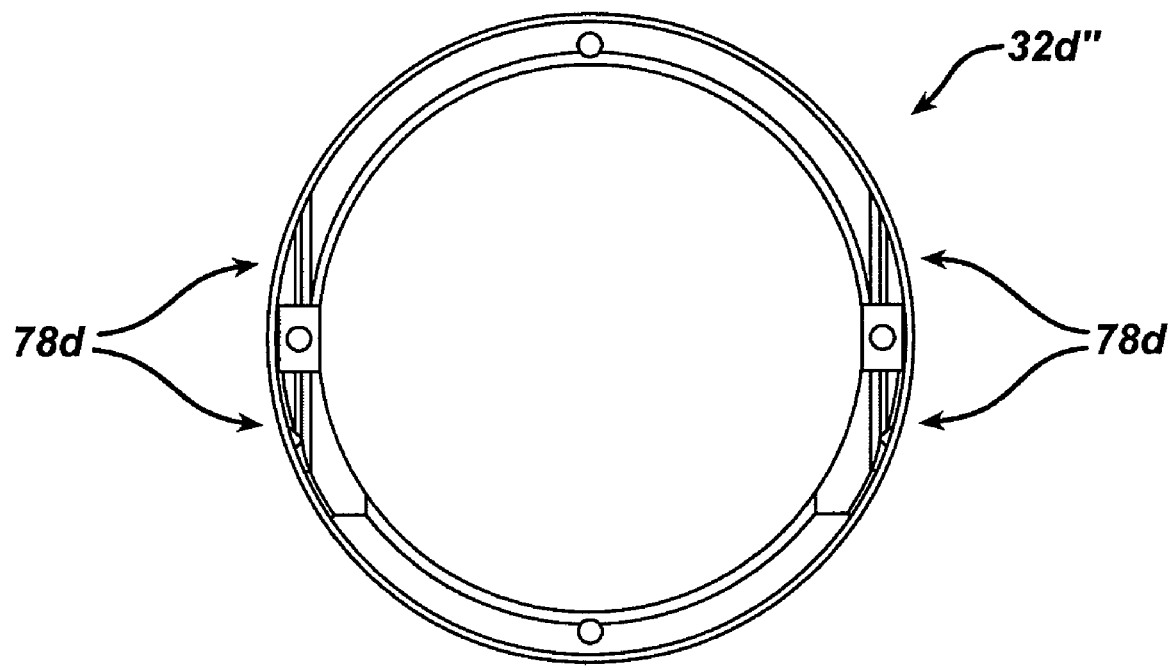
FIG. 34 is a proximal end view of the distal end link of FIG. 30.

An alternate exemplary embodiment of a steering platform 14" and various exemplary embodiments of components thereof are illustrated in FIGS. 21-34. The steering platform 14" can be fixedly or removably coupled to an elongate shaft similar to the shaft 12 discussed above, and can similarly be disposed in an outer sheath. The alternate steering platform's connector elements 28" and linearly arranged intermediate, proximal, and distal links 32i''', 32p''', 32d''' can have sizes and shapes such that at least when the steering platform 14" is in a resting position, e.g., as shown in FIG. 21 (connector elements 28" omitted but actuating cables 33" illustrated), facing convex surfaces of adjacent links are configured to contact each other, e.g., abut each other and not be separated by a distance, while facing concave surfaces of adjacent links are configured to be separated from each other by a distance. The steering platform 14" can nevertheless bend by having each convex surface of its various links 32i''', 32p''', 32d''' respectively include a beveled edge 78i, 78p, 78d configured to engage a beveled edge 78a, 78b, 78c on an adjacent link when the steering platform 14" bends. The facing concave surfaces of adjacent links, in this or other embodiments of a steering platform, can be configured to contact each other when the steering platform bends. The various links 32i''', 32p''', 32d''' can thus provide the steering platform 14" with a desirable curvature, e.g., up to about 75° in each available direction of steerable motion as mentioned above for the first embodiment of the steering platform 14. The steering platform 14" could thus have the same number of links as the first steering platform 14 but be more compact with a shorter longitudinal length. Further, the alternate steering platform 14" could have the same longitudinal length as the first steering platform 14 but include one or more additional links and one or more additional connector elements and thereby allow for more controlled, tighter articulation with the alternate steering platform 14" having a larger radius of curvature than the first steering platform 14 of equal longitudinal length.

The alternate steering platform 14" and its various components are similar to the first embodiment of the steering platform 14 and its various components discussed above and thus they will not be described in detail. As mentioned above, one difference between the two steering platforms 14, 14" includes the beveled edges 78i, 78p, 78d of the alternate links 32i''', 32p''', 32d'''. The beveled edges 78i, 78p, 78d of the alternate links 32i''', 32p''', 32d''' can be configured in any way, same or different from any other beveled edge of the steering platform 14". A person skilled in the art will appreciate that any one or more of the beveled edges 78i, 78p, 78d can include a chamfered edge and/or can include a plurality of beveled edges 78i, 78p, 78d. Another difference between the two steering platforms 14, 14" is that to accommodate the more closely linearly arranged links 32i''', 32p''', 32d''', a longitudinal length of the connector elements 28" of the alternate steering platform 14" can be shorter than the otherwise similar connector elements 28 discussed above.

In other embodiments, the various devices disclosed herein can include a locking mechanism for locking the handle(s) and/or actuator in a fixed position to maintain the working end of a surgical device, e.g., a steering platform, in desired articulated or angular orientation. While the locking mechanism can have a variety of configurations, in one exemplary embodiment the locking mechanism can be in the form of a clamp that is effective to clamp down onto one or more actuation cables and thereby prevent movement of the cables to lock the working end in a desired orientation. The clamp can have a variety of shapes and sizes, and it can be positioned at various locations on the device. Non-limiting examples of clamps can be found in previously mentioned U.S. Patent Publication No. 2007/0225562 titled "Articulating Endoscopic Accessory Channel" filed Mar. 23, 2006. In some embodiments, the cables can be used to passively allow articulation of the elongate shaft through a body of a patient, e.g., through a tortuous pathway, and the clamp or other locking mechanism can be used to lock the working end of the device into position when desired. In such a configuration, the handle can merely be used to facilitate grasping of the device.

Figure 35:
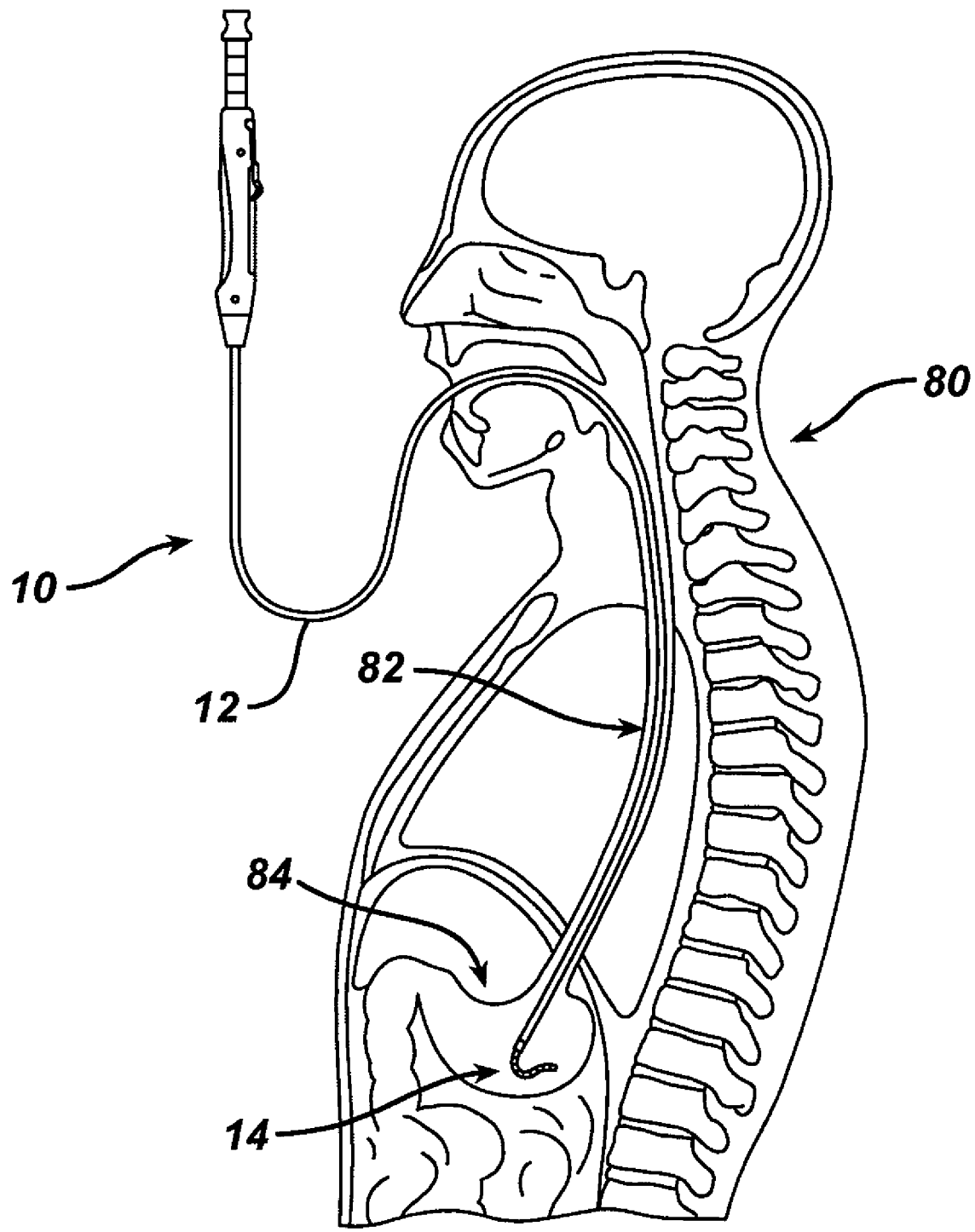
FIG. 35 is a perspective partially transparent view of the device of FIG. 1 transorally introduced into a patient.
Figure 36:
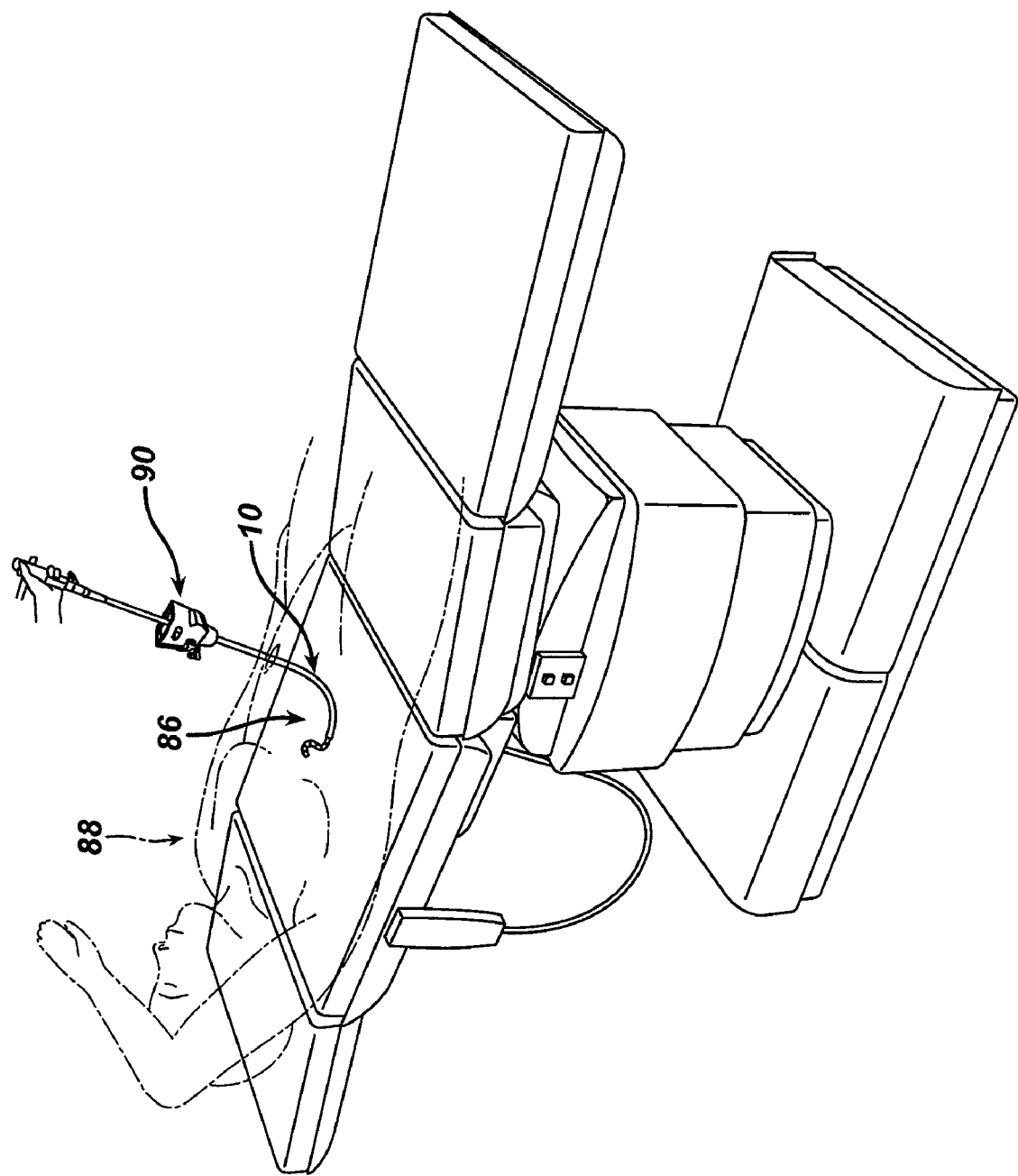
FIG. 36 is a perspective partially transparent view of the device of FIG. 1 introduced through a trocar into an abdomen of a patient.

In use, any of the surgical devices having a steering platform described herein can be introduced into a body of a patient for use in a surgical procedure. The device can be introduced in a variety of ways, such as through a natural orifice, an incision, and/or a trocar, as will be appreciated by a person skilled in the art. FIG. 35 illustrates an exemplary embodiment of the device 10 transorally introduced into a patient 80, with the steering platform 14 and at least a portion of the shaft 12 advanced through an esophagus 82 of the patient 80 into a stomach 84 in an abdominal cavity of the patient 80. FIG. 36 illustrates another exemplary embodiment with the device 10 being percutaneously introduced into an abdomen 86 of a patient 88 through a trocar 90.

A person skilled in the art will appreciate that the present invention has application in conventional endoscopic and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
    a flexible steering platform configured to receive a distal end of a flexible surgical instrument in a central passageway extending through the steering platform, the steering platform having
        a plurality of links each having a central bore such that the central bores define the central passageway,
        a plurality of substantially flat flexible connector elements, adjacent links being connected with at least two of the connector elements such that flexing at least two of the connector elements can bend the steering platform in at least two planes of motion; and
    first and second actuating cables extending at least partially through each of the plurality of links, wherein at least one of the first and second actuating cables extends at least partially through each of the plurality of flexible connector elements.

2. The device of claim 1, wherein the at least two planes of motion are substantially perpendicular.

3. The device of claim 1, wherein the first actuating cable is configured to bend the steering platform in a first plane of motion and the second actuating cable is configured to bend the steering platform in a second plane of motion.

4. The device of claim 1, further comprising third and fourth actuating cables extending at least partially through each of the plurality of links, wherein the first, second, third and fourth actuating cables are spaced equidistantly around the central passageway.

5. The device of claim 1, further comprising an elongate body having an inner lumen extending therethrough, wherein the elongate body is connected to a proximal end of the steering platform and the inner lumen is in communication with the central passageway.

6. The device of claim 1, wherein each of the links includes at least one recess, each recess having one of the connector elements disposed therein.

7. A surgical device, comprising:
    a steering segment having an outer sheath disposed over a steering platform, the steering platform being bendable and having
        a proximal base ring,
        a distal end ring,
        a plurality of separate links located between the proximal base ring and the distal end ring, each of the links in the form of a ring having at least two cutouts formed in a sidewall thereof, wherein the links are arranged consecutively along a length of the steering segment between the base ring and the end ring so as to define an inner lumen extending through the base ring, the end ring, and the links, and
        a plurality of flexible connector elements, at least two of the connector elements connecting adjacent links by having opposed proximal and distal end portions of each of the connector elements disposed in the cutouts such that each of the links has at least two connector elements connected thereto and disposed in cutouts formed therein.

8. The device of claim 7, wherein the steering segment is bendable in at least four directions.

9. The device of claim 7, wherein the proximal base ring is configured to be removably connected to a distal end of a cannulated elongate body, the elongate body configured to receive a surgical instrument therein.

10. The device of claim 7, further comprising at least one actuating cable extending through the plurality of separate links and the plurality of flexible connector elements.

11. The device of claim 10, wherein each link has at least one link bore formed axially therethrough, each connector element has at least one connector bore formed axially therethrough, and the link bores and the connector bores are aligned such that the at least one actuating cable extends through the at least one link bore in each link and through the at last one connector bore in each connector element.

12. A surgical device, comprising:
    a bendable steering platform configured to receive a distal end of a bendable surgical instrument disposed in a central passageway of the steering platform, the steering platform having
        a proximal base link having a distal side with at least two opposed concave end surfaces and at least two convex end surfaces,
        a distal end link having a proximal side with at least two opposed concave end surfaces and at least two opposed convex end surfaces,
        a plurality of intermediate links located between the proximal base link and the distal end link, each of the intermediate links having a proximal side with at least two opposed concave surfaces and at least two convex surfaces and a distal side with at least two opposed concave surfaces and at least two convex surfaces, wherein the convex surfaces on the proximal side have beveled edges, the convex surfaces on the distal side have beveled edges, the base link, the end link, and the intermediate links are linearly arranged, and the beveled edges of adjacent links contact each other at least when a longitudinal axis of the central passageway is substantially straight, and
    a plurality of flexible connector elements, at least two of the connector elements connecting adjacent links.

13. The device of claim 12, further comprising an actuating cable extending at least partially through each of the plurality of links and each of the plurality of connector elements such that actuating the actuating cable can bend the bendable steering platform such that at least one of the concave surfaces on the proximal side of a first one of the links moves toward at least one of the concave surfaces on the distal side of a second one of the links that is adjacent to the first one of the links.

14. The device of claim 12, wherein the at least two opposed convex surfaces on the proximal sides of the intermediate links face the at least two opposed convex surfaces on the distal side of an adjacent one of the proximal link or intermediate links.

15. The device of claim 12, wherein the connector elements couple to the convex surfaces of adjacent links.

16. The device of claim 12, wherein the concave surfaces of adjacent links are separated by a distance at least when a longitudinal axis of the central passageway is substantially straight.

17. A surgical method, comprising:
introducing a surgical instrument having a steering segment at a distal end thereof into a patient, the steering segment including
a plurality of links each having first and second holes formed in a wall thereof,
a plurality of axially aligned flexible connector elements each having first and second tabs and each having first bores formed therethrough, at least two of the plurality of connector elements connecting adjacent ones of the plurality of links by seating the first and second tabs in cutouts formed in sidewalls of the adjacent ones of the plurality of links such that the bores of the connector elements align with the first holes of the links,
a first actuating cable extending through each of the bores and the first holes, and
a second actuating cable extending through each of the second holes;
actuating at least one of the actuating cables to bend the steering segment and the distal end of the surgical instrument.

18. The device of claim 1, wherein the plurality of flexible connector elements have a first end, a second end, and an intermediate portion extending therebetween, wherein a first width of the first end and a second width of the second end are each greater than a third width of the intermediate portion.

19. The device of claim 18, wherein the first, second, and third widths are substantially non-varying when the steering platform is bent in the at least two planes of motion.

* * * * *